United States Patent [19]

Katoh et al.

[11] Patent Number: 4,609,619

[45] Date of Patent: Sep. 2, 1986

[54] LIGHT-SENSITIVE SILVER HALIDE COLOR PHOTOGRAPHIC MATERIAL

[75] Inventors: Katsunori Katoh; Satoshi Nakagawa, both of Hino, Japan

[73] Assignee: Konishiroku Photo Industry Co., Ltd., Tokyo, Japan

[21] Appl. No.: 774,892

[22] Filed: Sep. 11, 1985

[30] Foreign Application Priority Data

Sep. 17, 1984 [JP] Japan .................. 59-195233
Sep. 21, 1984 [JP] Japan .................. 59-198154

[51] Int. Cl.$^4$ .................................. G03C 1/40
[52] U.S. Cl. ........................... 430/553; 430/552
[58] Field of Search .................. 430/552, 553

[56] References Cited

U.S. PATENT DOCUMENTS 4,465,766  8/1984  Sato et al. ................. 430/552
4,518,683  5/1985  Kato et al. ................ 430/552
4,551,422 11/1985  Kimura et al. ............ 430/552

FOREIGN PATENT DOCUMENTS 0097042 12/1983 European Pat. Off. ........ 430/552
0180559 10/1984 Japan .......................... 430/553

*Primary Examiner*—Richard L. Schilling
*Attorney, Agent, or Firm*—Frishauf, Holtz, Goodman & Woodward

[57] ABSTRACT

A light-sensitive silver halide color photographic material, which comprises a cyan coupler for photography represented by the formula [IA] or [IB] shown below in the light-sensitive emulsion;

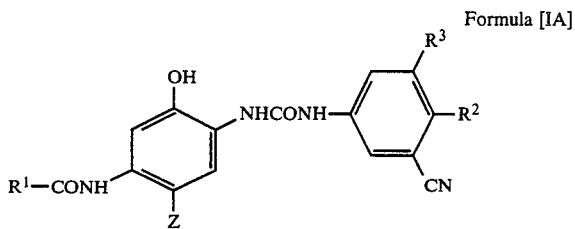

Formula [IA]

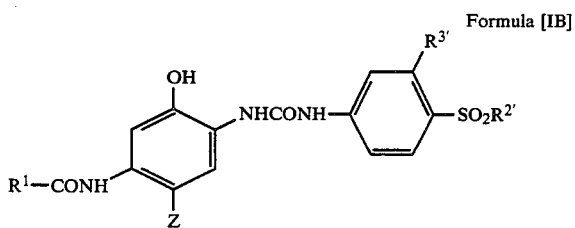

Formula [IB]

wherein $R^1$ is a group having a bulk sufficient to impart diffusion resistance to said coupler; $R^2$ and $R^3$ each represent a hydrogen atom or a halogen atom, at least one of $R^2$ and $R^3$ being a halogen atom; $R^{2'}$ represents an alkyl group, a cycloalkyl group, an alkenyl group or an aryl group; $R^{3'}$ represents a halogen atom; and Z represents a hydrogen atom or a group eliminable during the coupling reaction with the oxidized product of a color developing agent.

According to the material of this invention, good spectral absorption characteristics can be exhibited and a cyan dye image can be given without dye loss even by use of a bleaching bath or bleach fixing bath which is fatigued after running.

14 Claims, 2 Drawing Figures

LIGHT-SENSITIVE SILVER HALIDE COLOR PHOTOGRAPHIC MATERIAL

BACKGROUND OF THE INVENTION

This invention relates to a light-sensitive silver halide color photographic material, particularly to a light-sensitive silver halide color photographic material which can exhibit good spectral absorption characteristics and give a cyan dye image without dye loss even by use of a bleaching bath or bleach-fixing bath which is fatigued after running.

As usual, in a light-sensitive silver halide color photographic material, silver halide grains exposed to light are reduced with an aromatic primary amine type color developing agent, and a dye image can be obtained through coupling of the oxidized product of said color developing agent thereby formed, with a coupler for forming each of yellow, magenta and cyan dyes.

The coupler widely used for formation of the above cyan dye is a phenol type or naphthol type cyan coupler.

In the field of photography in recent years, with rapid development of color photograhic techniques, the amount of color nega films processed has become so enormous that the phenomenon occurs in which bleaching bath or bleach-fixing bath is fatigued in running.

The naphthol type compound which has been widely used as the cyan coupler for color nega film is found to involve the drawback that, when processed with a fatigued bleaching bath or bleach-fixing bath, the dye once formed is returned to the leuco form, thereby causing dye loss. For improving these drawbacks, as disclosed in Japanese Unexamined Patent Publications Nos. 21139/1972, 65134/1981, 204543/1982, 204544/1982, 204545/1982, 98731/1983, 187928/1983, cyan couplers having a phenylureido group at the 2-position of phenol have been developed, whereby the dye loss could be improved dramatically. On the other hand, since these couplers are relatively shorter in the maximum absorption wavelength as compared with naphthol type couplers, absorption at the green light region on the shorter wavelength region is greater, which is not preferable in color reproduction. Visual sensitivity of human beings is most sensitive particularly to green light and even a slight reduction in such an unnecessary absorption can bring about a great visual improvement. Thus, it has been desired to have a further improvement.

SUMMARY OF THE INVENTION

A first object of the present invention is to provide a light-sensitive silver halide photographic material which is good in spectral absorption characteristics and can give a cyan dye image formed at relatively longer wavelengths.

A second object of the present invention is to provide a light-sensitive silver halide photographic material which can give a cyan image without dye loss even by use of a bleaching bath or a bleach-fixing bath which is fatigued after running.

A third object of the present invention is to provide a light-sensitive silver halide photographic material having high sensitivity and forming a cyan image which can give a high color forming density.

A fourth object of the present invention is to provide a light-sensitive silver halide photographic material forming a cyan image which can be produced at relatively low cost.

A fifth object of the present invention is to provide a light-sensitive silver halide photographic material which can give a cyan image excellent in dispersion stability.

The above objects of the present invention have been accomplished by incorporating in the light-sensitive emulsion layer a cyan coupler for photography represented by the formula [IA] or [IB] shown below:

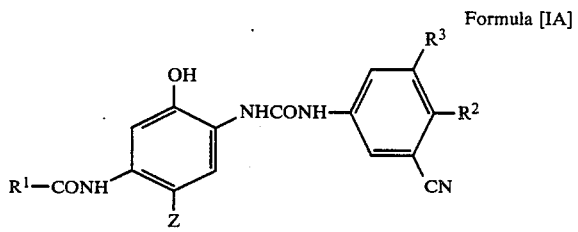

Formula [IA]

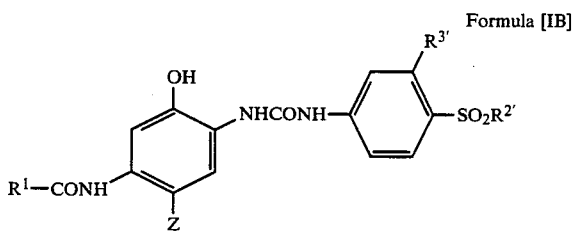

Formula [IB]

wherein $R^1$ is a group sufficient to impart diffusion resistance to said coupler; $R^2$ and $R^3$ each represent a hydrogen atom or a halogen atom, at least one of $R^2$ and $R^3$ being a halogen atom; $R^{2'}$ represents an alkyl group, a cycloalkyl group, an alkenyl group or an aryl group; $R^{3'}$ represents a halogen atom; and Z represents a hydrogen atom or a group eliminable during the coupling reaction with the oxidized product of a color developing agent.

DESCRIPTION OF THE PREFERRED EMBODIMENTS

Figure 1:
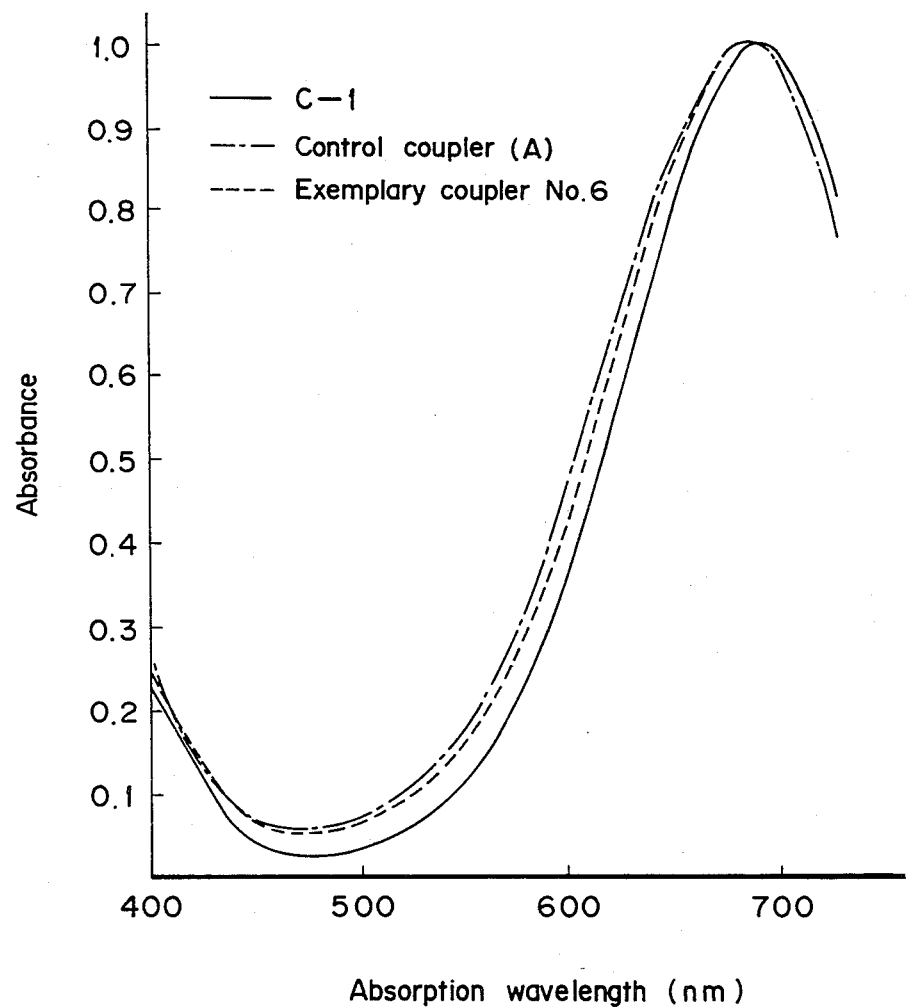
FIG. 1 and FIG. 2 show graphs of spectral absorption characteristics of dyes formed by various kinds of couplers.
Figure 2:
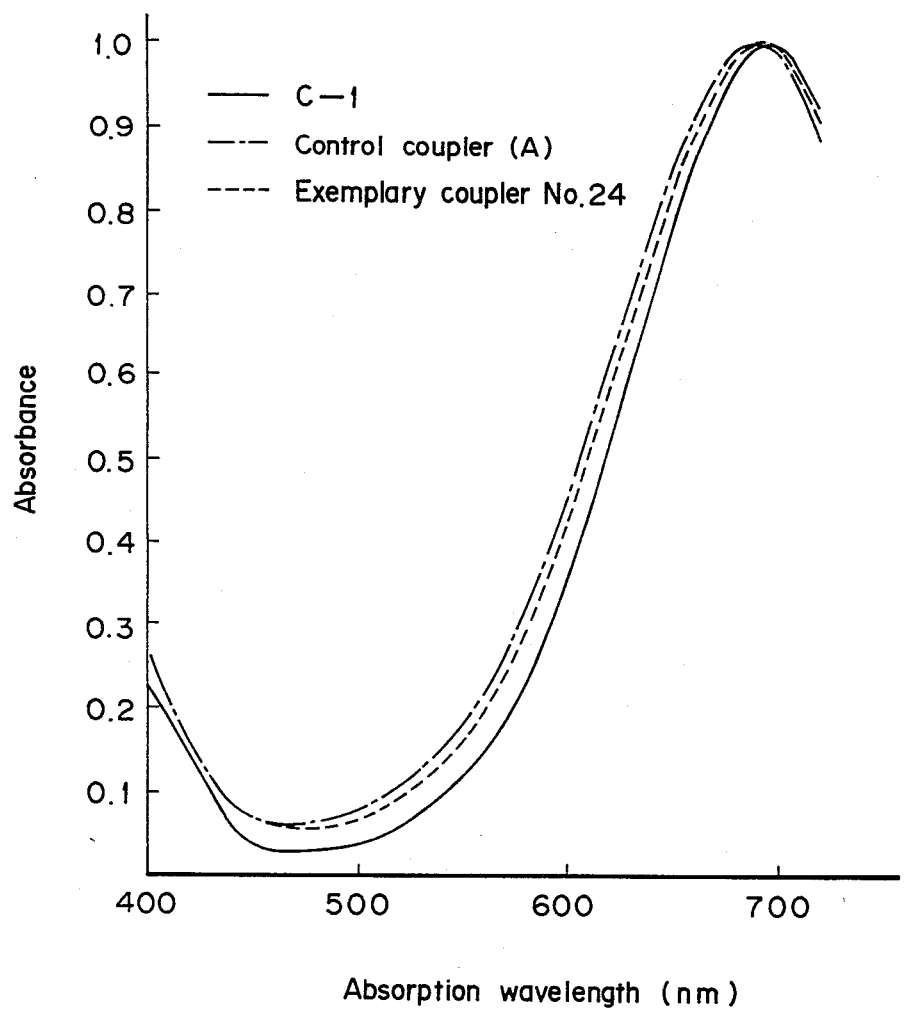

In the present invention, $R^1$ in Formulae [IA] and [IB] represents an alkyl group or an aryl group. The alkyl group may be an alkyl group having 1 to 20 carbon atoms, which may have substituents, preferably a group of the Formula [II]:

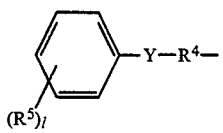

wherein Y represents —O—, —S— or —SO$_2$—; $R^4$ represents an alkylene group having 1 to 20 carbon atoms (e.g. methylene, 1,1-ethylene, 1,1-propylene, 1,3-propylene, 2-methyl-1,1-propylene, 1,1-pentylene, 1,1-heptylene, 1,1-nonylene, 1,1-undecylene, 1,1-tridecylene, 1,1-pentadecylene, etc.); $R^5$ represents a halogen atom (e.g. chlorine atom, fluorine atom, etc.), a hydroxy group, an alkyl group having 1 to 20 carbon atoms (e.g.

methyl, ethyl, tert-butyl, tert-pentyl, cyclopentyl, tert-octyl, pentadecyl, etc.), an alkoxy group (e.g. methoxy, ethoxy, isopropoxy, butoxy, hexyloxy, dodecyloxy, etc.), an alkyl sulfonamide group (e.g. methanesulfonamide, ethanesulfonamide, butanesulfonamide, octylsulfonamide, hexadecylsulfonamide, etc.), an arylsulfonamide group (e.g. benzenesulfonamide, m-chlorobenzenesulfonamide, toluenesulfonamide, p-methoxybenzenesulfonamide, p-dodecyloxybenzenesulfonamide, etc.), an alkylsulfamoyl group (e.g. butylsulfamoyl, tert-butylsulfamoyl, dodecylsulfamoyl, etc.)a, an arylsulfamoyl group (e.g. benzenesulfamoyl, toluenesulfamoyl, dodecyloxybenzenesulfamoyl, etc.), an alkylsulfonyl group (e.g. methanesulfonyl, butanesulfonyl, etc.), an arylsulfonyl group (e.g. benzenesulfonyl, p-benzyloxyphenylsulfonyl, p-hydroxyphenylsulfonyl, etc.), a cycloalkyl group (e.g. cyclopentyl), an alkoxycarbonyl group (e.g. ethoxycarbonyl, butoxycarbonyl, hexadecyloxycarbonyl, etc.) and so on; l represents an integer of 1 to 4, prefeably 1 or 2; when l is 2 or more, $R^5$ may be either identical or different.

In the present invention, when $R^1$ in Formula [IA] or [IB] is an aryl group, it should preferably a phenyl group, and said phenyl group may be substituted with $R^5$ shown in the above Formula [II].

In the present invention, Z in the above Formula [IA] and [IB] represents a hydrogen atom or a group eliminable during the coupling reaction with the oxidized product of a color forming developing agent, and such a group is well known to those skilled in the art. Also, such a group can control the reactivity of the coupler and, after being released from the coupler, also can perform the functions such as developing inhibition, bleaching inhibition, bleaching acceleration, color correction, etc., whereby advantageous effects can be brought about to its own layer or other layers.

As typical examples of such groups, there may be mentioned halogen atoms (chlorine atom, fluorine atom, etc.), alkoxy groups (methoxyethylaminocarbonylmethoxy, methanesulfonylethoxy, etc.), aryloxy groups (p-ethoxycarbonylphenoxy, p-methoxyphenoxy, p-butanesulfonamidophenoxy, p-β-carboxy propaneamidophenoxy, etc.), arylthio groups (o-butoxyphenylthio, p-tert-butylphenylthio, m-butanesulfonamidophenylthio, etc.). These groups eliminable during coupling are disclosed in, for example, U.S. Pat. Nos. 2,455,169; 3,227,551; 3,432,521; 3,476,563; 3,617,291; 3,880,661; 4,052,212; and 4,134,766; U.K. Patents and Unexamined Patent Publications 1,466,728; 1,531,927; 1,533,039; 2,006,755 and 2,017,704.

In the present invention, $R^2$ and $R^3$ in Formula [IA] each represent a hydrogen atom or a halogen atom, and the halogen atom may include fluorine atom, chlorine atom, bromine atom, etc., preferably chlorine atom.

In the present invention, $R^{2'}$ in Formula [IB] represents an alkyl group, a cycloalkyl group, an alkenyl group or an aryl group. The alkyl group may be an alkyl group having 1 to 20 carbon atoms (e.g. methyl, ethyl, iso-propyl, propyl, butyl, tert-butyl, hexyl, methoxymethyl, ethoxyethyl, ethoxycarbonylmethyl, methanesulfonylethyl, benzyl, phenethyl, dodecyl, etc.), preferably an alkyl group having 1 to 8 carbon atoms. The cycloalkyl group may include, for example, cyclopropyl, cyclopentyl, cyclohexyl, etc.; the alkenyl group, for example, vinyl, 2-propenyl, isopropenyl, butenyl, hexenyl, etc.; and the aryl group, for example, phenyl, p-hydroxyphenyl, p-methoxyphenyl, m-chlorophenyl, etc.

In the present invention, $R^{3'}$ shown in Formula [IB] represents a halogen atom, preferably a chlorine atom.

The cyan coupler preferably used in the present invention may be represented by Formula [IIIA] or [IIIB] shown below:

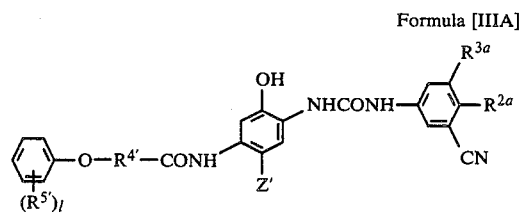

Formula [IIIA]

wherein $R^{2a}$ and $R^{3a}$ each represent a hydrogen atom or a chlorine atom; $R^{4'}$ an alkylene group having 1 to 20 carbon atoms; $R^{5'}$ a hydroxy group or an alkyl group having 1 to 20 carbon atoms; $Z'$ a hydrogen atom, a halogen atom or an aryloxy group; at least one of $R^{2a}$ and $R^{3a}$ being a chlorine atom; l is an integer of 1 or 2; when l is 2, both $R^{5'}$ may be either identical or different; the total number of carbon atoms in the alkylene group represented by $R^{4'}$ and the alkyl group represented by $R^5$ may preferably be 8 to 25.;

Formula [IIIB]

wherein $R^{2b}$ represents an alkyl group having 1 to 8 carbon atoms; $R^{3b}$ a chlorine atom; $R^{4'}$ an alkylene group having 1 to 20 carbon atoms; $R^{5'}$ a hydroxy group, an alkyl group having 1 to 20 carbon atoms or a cycloalkyl group; $Z'$ a hydrogen atom, a halogen atom or an aryloxy group; l is an integer of 1 or 2; when l is 2, both $R^{5'}$ may be either identical or different; the total number of carbon atoms in the alkylene group represented by $R^{4'}$ and the alkyl group represented by $R^{5'}$ may preferably be 8 to 25.

Typical examples of the cyan couplers of the present invention are set forth below, but the present invention is not limited thereto.

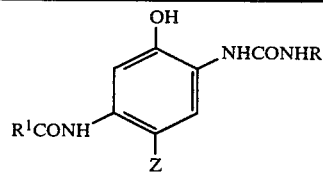

| Exemplary coupler No. | $R^1$ | R | Z |
|---|---|---|---|
| 1 | $C_{15}H_{31}$—C₆H₄—OCH($C_2H_5$)— | 3-Cl, 4-CN-phenyl | H |
| 2 | 2,4-di(t)$C_5H_{11}$-C₆H₃—OCH($C_2H_5$)— | 3-Cl, 4-CN-phenyl | H |
| 3 | 3-(t)$C_4H_9$-4-HO-C₆H₃—OCH($C_{12}H_{25}$)— | 3-F, 4-CN-phenyl | Cl |
| 4 | 2,4-di(t)$C_5H_{11}$-C₆H₃—OCH($C_2H_5$)— | 3-Cl, 4-CN-phenyl | H |
| 5 | 2,4-di(t)$C_5H_{11}$-C₆H₃—OCH($C_2H_5$)— | 3-Cl, 4-CN-phenyl | Cl |
| 6 | 2,4-di(t)$C_5H_{11}$-C₆H₃—OCH($C_4H_9$)— | 3-Cl, 4-CN-phenyl | H |
| 7 | 2,4-di(t)$C_5H_{11}$-C₆H₃—OCH($C_4H_9$)— | 3-Cl, 4-CN-phenyl | Cl |
| 8 | 2,4-di(t)$C_5H_{11}$-C₆H₃—OCH($C_4H_9$)— | 3-Cl, 4-CN-phenyl | —O—C₆H₄—OCH₃ |
| 9 | 2,4-di(t)$C_4H_9$-C₆H₃—OCH($C_4H_9$)— | 3-Cl, 4-CN-phenyl | Cl |
| 10 | 2,4-di(t)$C_5H_{11}$-C₆H₃—OCH($C_3H_7(i)$)— | 3-Cl, 4-CN-phenyl | H |
| 11 | 3-(t)$C_4H_9$-4-HO-C₆H₃—OCH($C_{12}H_{25}$)— | 3-Cl, 4-CN-phenyl | H |

-continued

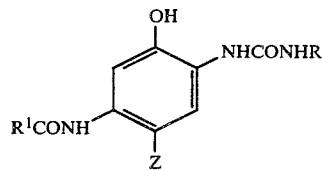

| Exemplary coupler No. | R¹ | R | Z |
|---|---|---|---|
| 12 | HO—⟨C₆H₄⟩—SO₂—⟨C₆H₄⟩—O—CH(C₁₀H₂₁)— | 2-Cl, 4-CN phenyl | H |
| 13 | ⟨C₆H₅⟩—CH₂O—⟨C₆H₄⟩—SO₂—⟨C₆H₄⟩—O—CH(C₁₀H₂₁)— | 2-Cl, 4-CN phenyl | H |
| 14 | HO—⟨C₆H₄⟩—SO₂—⟨C₆H₄⟩—O—CH(C₁₂H₂₅)— | 2-Cl, 4-CN phenyl | H |
| 15 | 4-CH₃, 2-C₁₀H₂₁ phenyl—O—CH(C₂H₅)— | 2-Cl, 4-CN phenyl | H |
| 16 | 4-(t)C₄H₉, 2-cyclopentyl phenyl—O—CH(C₂H₅)— | 2-Cl, 4-CN phenyl | H |
| 17 | 2,4-di(t)C₅H₁₁ phenyl—O—CH(C₂H₅)— | 2,3-di-Cl, 4-CN phenyl | H |
| 18 | C₁₅H₃₁—⟨C₆H₄⟩—O—CH(C₂H₅)— | 2-Cl, 4-SO₂C₂H₅ phenyl | H |
| 19 | 2,4-di(t)C₅H₁₁ phenyl—OCH₂— | 2-Cl, 4-SO₂C₃H₇ phenyl | Cl |
| 20 | 2,4-di(t)C₅H₁₁ phenyl—O—CH(C₂H₅)— | 2-Cl, 4-SO₂CH₃ phenyl | H |
| 21 | 2,4-di(t)C₅H₁₁ phenyl—O—CH(C₄H₉)— | 2-Cl, 4-SO₂CH₂—⟨C₆H₅⟩ phenyl | Cl |
| 22 | 4-HO, 3-(t)C₄H₉ phenyl—O—CH(C₁₀H₂₁)— | 2-Cl, 4-SO₂C₂H₅ phenyl | H |

-continued

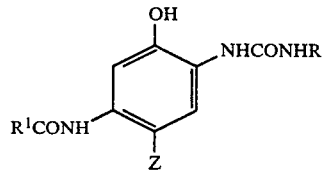

| Exemplary coupler No. | R¹ | R | Z |
|---|---|---|---|
| 23 | HO–⟨C₆H₃(t)C₄H₉⟩–OCH(C₁₂H₂₅)– | –⟨C₆H₃(Cl)⟩–SO₂C₂H₅ | Cl |
| 24 | (t)C₅H₁₁–⟨C₆H₃(C₅H₁₁(t))⟩–OCH(C₂H₅)– | –⟨C₆H₃(Cl)⟩–SO₂C₂H₅ | H |
| 25 | (t)C₅H₁₁–⟨C₆H₃(C₅H₁₁(t))⟩–OCH(C₂H₅)– | –⟨C₆H₃(Cl)⟩–SO₂C₂H₅ | Cl |
| 26 | (t)C₅H₁₁–⟨C₆H₃(C₅H₁₁(t))⟩–OCH(C₂H₅)– | –⟨C₆H₃(Cl)⟩–SO₂CH₂–⟨C₆H₅⟩ | H |
| 27 | (t)C₅H₁₁–⟨C₆H₃(C₅H₁₁(t))⟩–OCH(C₂H₅)– | –⟨C₆H₃(Cl)⟩–SO₂CH₂CH₂–⟨C₆H₅⟩ | H |
| 28 | (t)C₅H₁₁–⟨C₆H₃(C₅H₁₁(t))⟩–OCH(C₂H₅)– | –⟨C₆H₃(Cl)⟩–SO₂C₂H₅ | –O–⟨C₆H₄⟩–OCH₃ |
| 29 | (t)C₅H₁₁–⟨C₆H₃(C₅H₁₁(t))⟩–OCH(C₂H₅)– | –⟨C₆H₃(Cl)⟩–SO₂–⟨C₆H₁₁⟩ | H |
| 30 | (t)C₅H₁₁–⟨C₆H₃(C₅H₁₁(t))⟩–OCH(C₃H₇(i))– | –⟨C₆H₃(Cl)⟩–SO₂CH₂CH₂CH₃ | Cl |
| 31 | (t)C₅H₁₁–⟨C₆H₃(C₅H₁₁(t))⟩–OCH(C₁₂H₂₅)– | –⟨C₆H₃(Cl)⟩–SO₂C₄H₉(t) | H |
| 32 | (t)C₄H₉–⟨C₆H₄⟩–SO₂CH(C₁₂H₂₅)– | –⟨C₆H₃(Cl)⟩–SO₂C₂H₅ | Cl |
| 33 | (t)C₅H₁₁–⟨C₆H₃(C₅H₁₁(t))⟩–OCH(C₃H₇(i))– | –⟨C₆H₃(Cl)⟩–SO₂C₃H₇(i) | H |

-continued

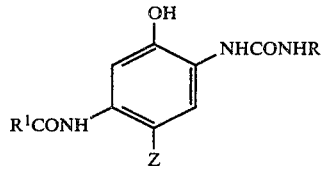

| Exemplary coupler No. | $R^1$ | R | Z |
|---|---|---|---|
| 34 | (t)$C_5H_{11}$—⌬($C_5H_{11}$(t))—O$\underset{C_8H_{17}}{CH}$— | —⌬(Cl)—$SO_2CH_2COOC_2H_5$ | H |
| 35 | (t)$C_5H_{11}$—⌬($C_5H_{11}$(t))—O$\underset{C_4H_9}{CH}$— | —⌬(Cl)—$SO_2C_5H_{11}$ | H |
| 36 | (t)$C_4H_9$—⌬($C_4H_9$(t))—O$\underset{C_2H_5}{CH}$— | —⌬(Cl)—$SO_2C_4H_9$ | H |
| 37 | (t)$C_4H_9$—⌬(H)—O$\underset{C_4H_9}{CH}$— | —⌬(Cl)—$SO_2C_4H_9$ | Cl |

The cyan coupler of the present invention can be synthesized easily according to the methods known in the art. In the following, synthesis examples in general are shown.

SYNTHESIS EXAMPLE 1 (Synthesis of Exemplary coupler No. 6)

(A) Synthesis of 2-(4-chloro-3-cyano)phenylureido-5-nitrophenol:

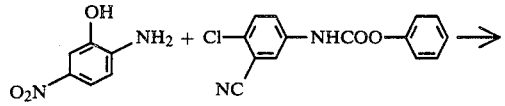

-continued

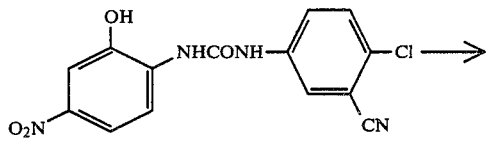

Into 300 ml of toluene were added 15.4 g of 2-amino-5-nitrophenol, 27.3 g of 4-chloro-3-cyanophenylphenyl-carbamate and 0.7 g of imidazole, and the mixture was boiled under reflux for 5 hours. The reaction mixture was left to cool to room temperature, and the precipitated crystals were filtered off and washed with methanol, to obtain 20.1 g of yellow crystals (Yield: 60.4%).

(B) Synthesis of Exemplary coupler No. 6:

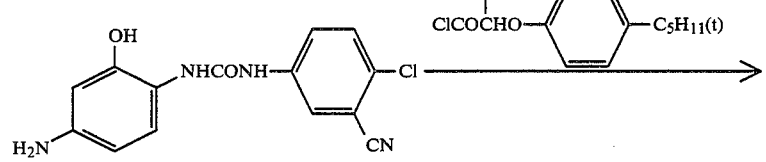

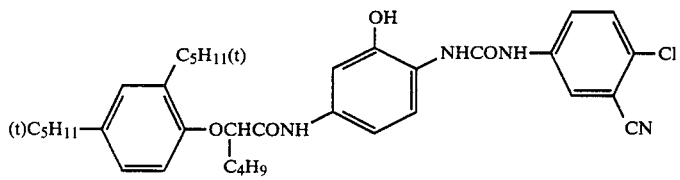

After 16.6 g of 2-(4-chloro-3-cyano)phenylureido-5-nitrophenol was dispersed in 300 ml of tetrahydrofuran, hydrogenation was carried out under normal pressure with the use of Raney-nickel catalyst. After consumption of the theoretical amount of hydrogen, Raney-nickel catalyst was filtered off. To the filtrate were added 4.7 g of pyridine and 20.2 g of α-(2,4-di-tert-amyl)phenoxyhexanoyl chloride, and the mixture was stirred under room temperature for one hour. Tetrahydrofuran was evaporated from the reaction mixture under reduced pressure, water was added to the residue and the mixture was extracted with ethyl acetate. The oil layer was washed with water and, after separation of the aqueous layer, ethyl acetate was evaporated off under reduced pressure and the residue was purified by use of a silica gel column chromatography. Crystallization from acetonitrile gave 24.1 g of white powder. The structure was measured by NMR and MASS to identify the title product.

SYNTHESIS EXAMPLE 2 (Synthesis of Exemplary coupler No. 7)

(A) Synthesis of 2-(4-chloro-3-cyanophenyl)ureido-4-chloro-5-nitrophenol:

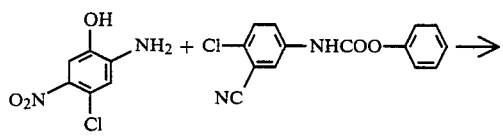

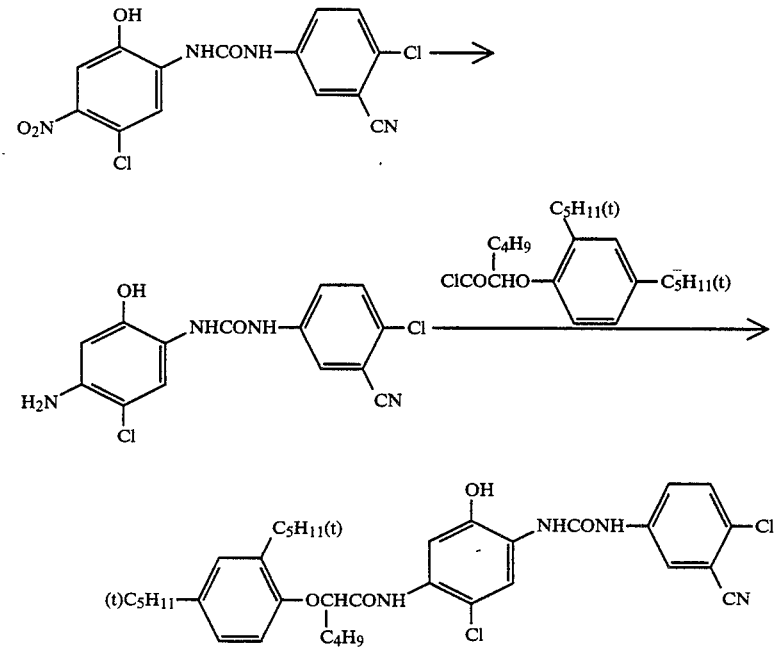

Into 300 ml of toluene were added 18.9 g of 2-amino-4-chloro-5-nitrophenol, 27.3 g of 4-chloro-3-cyano-phenylphenylcarbamate and 0.9 g of imidazole, and the mixture was boiled under reflux for 5 hours. The reaction mixture was left to cool to room temperature, and the precipitated crystals were filtered off and washed with methanol, to obtain 23.5 g of yellow crystals (Yield: 64.0%).

(B) Synthesis of Exemplary coupler No. 7:

After 18.4 g of 2-(4-chloro-3-cyanophenyl)ureido-4-chloro-5-nitrophenol was dispersed in 300 ml of tetrahydrofuran, hydrogenation was carried out under normal pressure with the use of Raney-nickel catalyst. After consumption of the theoretical amount of hydrogen, Raney-nickel catalyst was filtered off. To the filtrate were added 4.7 g of pyridine and 20.2 g of α-(2,4-di-tert-amyl)phenoxyhexanoyl chloride, and the mixture was stirred under room temperature for one hour. Tetrahydrofuran was evaporated from the reaction mixture under reduced pressure, water was added to the residue and the mixture was extracted with ethyl acetate. The oil layer was washed with water and, after separation of the aqueous layer, ethyl acetate was evaporated off under reduced pressure and the residue was purified by use of a silica gel column chromatography. Crystallization from acetonitrile gave 22.0 g of white powder. The structure was measured by NMR and MASS to identify the title product.

SYNTHESIS EXAMPLE 3 (Synthesis of Exemplary coupler No. 24)

(A) Synthesis of 2-(3-chloro-4-ethanesulfonyl)-phenylureido-5-nitrophenol:

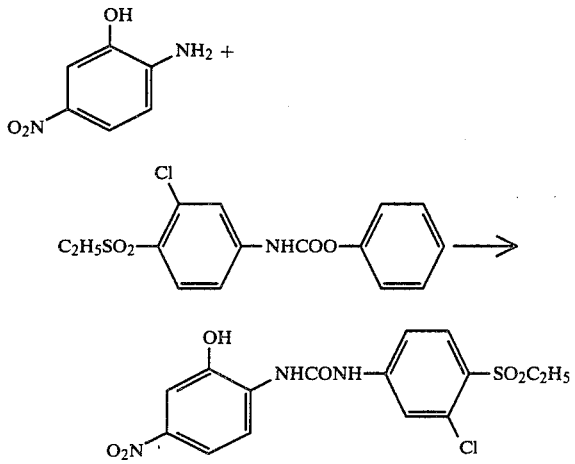

Into 300 ml of toluene were added 15.4 g of 2-amino-5-nitrophenol, 37.4 g of 3-chloro-4-ethanesulfonyl-phenylphenylcarbamate and 0.7 g of imidazole, and the mixture was boiled under reflux for 5 hours. The reaction mixture was left to cool to room temperature, and the precipitated crystals were filtered off and washed with methanol, to obtain 23 g of yellow crystals.

(B) Synthesis of Exemplary coupler No. 24:

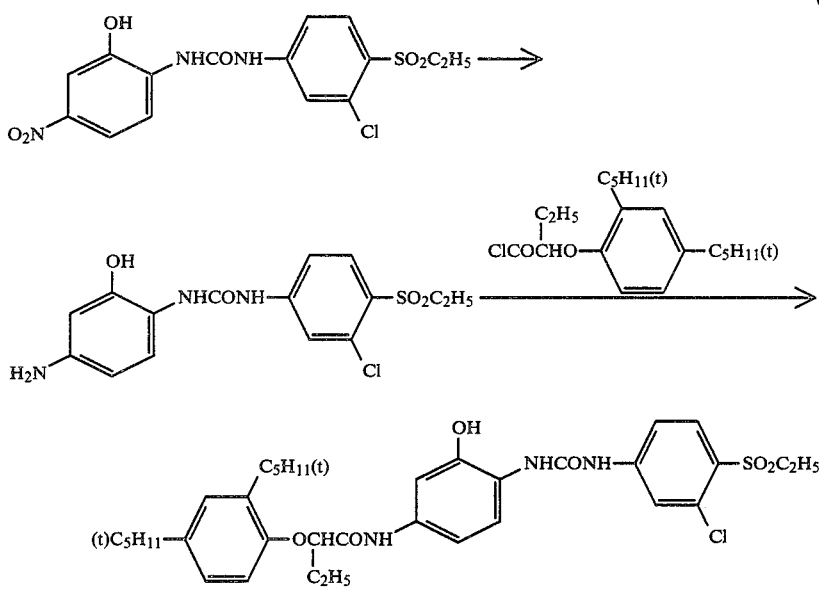

After 20 g of 2-(3-chloro-4-ethanesulfonyl)-phenylureido-5-nitrophenol was dispersed in 400 ml of tetrahydrofuran, hydrogenation was carried out under normal pressure with the use of Raney-nickel catalyst. After consumption of the theoretical amount of hydrogen, Raney-nickel catalyst was filtered off. To the filtrate were added 4.7 g of pyridine and 18.6 g of α-(2,4-di-tert-amyl)phenoxybutanoyl chloride, and the mixture was stirred under room temperature for one hour. Tetrahydrofuran was evaporated from the reaction mixture under reduced pressure, water was added to the residue and the mixture was extracted with ethyl acetate. The oil layer was washed with water and, after separation of the aqeuous layer, ethyl acetate was evaporated off under reduced pressure and the residue was purified by use of a silica gel column chromatography to give 15.3 g of a white caramel-like product. The structure was measured by NMR and MASS to identify the title product.

SYNTHESIS EXAMPLE 4 (Synthesis of Exemplary coupler No. 25)

(A) Synthesis of 2-(3-chloro-4-ethanesulfonyl)-phenylureido-4-chloro-5-nitrophenol:

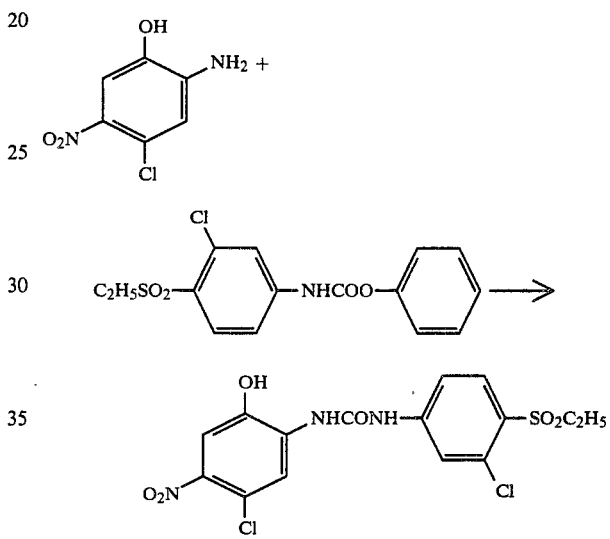

Into 300 ml of toluene were added 18.9 g of 2-amino-4-chloro-5-nitrophenol, 37.4 g of 3-chloro-4-ethanesulfonylphenyl-phenylcarbamate and 0.9 g of imidazole, and the mixture was boiled under reflux for 5 hours. The reaction mixture was left to cool to room temperature, and the precipitated crystals were filtered off and washed with methanol, to obtain 28.7 g of yellow crystals.

(B) Synthesis of Exemplary coupler No. 25:

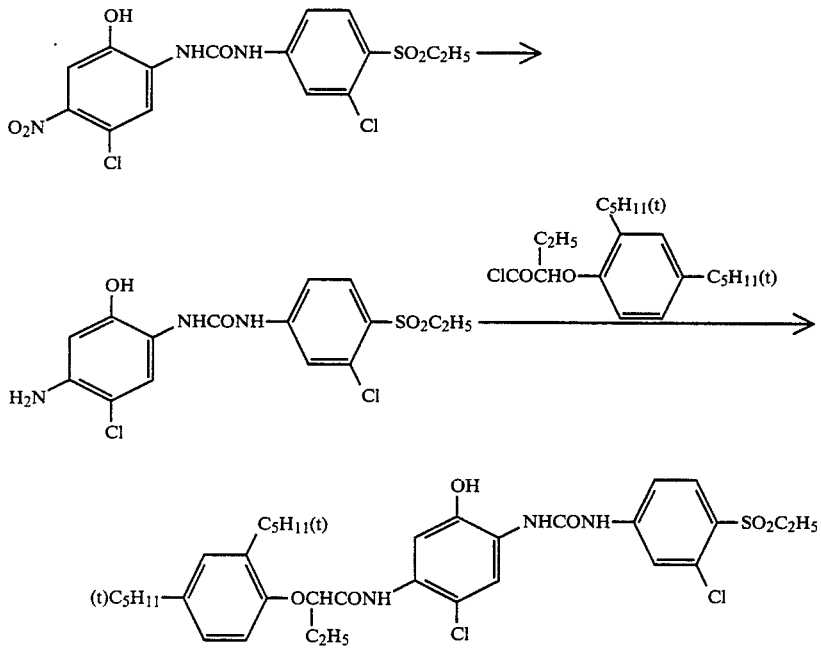

After 21.7 g of 2-(3-chloro-4-ethanesulfonyl)-phenyluriedo-4-chloro-5-nitrophenol was dispersed in 300 ml of tetrahydrofuran, hydrogenation was carried out under normal pressure with the use of Raney-nickel catalyst. After consumption of the theoretical amount of hydrogen, Raney-nickel catalyst was filtered off. To the filtrate were added 4.7 g of pyridine and 18.6 g of α-(2,4-di-tert-amyl)phenoxybutanoyl chloride, and the mixture was stirred under room temperature for one hour. Tetrahydrofuran was evaporated from the reaction mixture under reduced pressure, water was added to the residue and the mixture was extracted with ethyl acetate. The oil layer was washed with water and, after separation of the aqueous layer, ethyl acetate was evaporated off under reduced pressure and the residue was purified by use of a silica gel column chromatography to give 14.8 g of a white caramel-like product. The structure was measured by NMR and MASS to identify the title product.

The light-sensitive silver halide color photographic material prepared by use of the above coupler according to the present invention (hereinafter called the coupler of the present invention) may also contain dye forming couplers conventionally used in the prior art.

The cyan dye forming couplers to be used in the present invention can be used according to the same method and for the same purpose as employed in the photographic technique of the prior art.

Typically, the cyan coupler of the present invention may be contained in the silver halide emulsion layers and/or non-sensitive layers adjacent thereto. More specifically, the cyan coupler of the present invention may be formulated in a silver halide emulsion and the emulsion is applied on a support to give a light-sensitive silver halide color photographic material containing the coupler in the silver halide emulsion layer. The light-sensitive silver halide color photographic material may be either monochrome or multi-color. In the case of multi-color, the cyan coupler of the present invention is incorporated usually in the red-sensitive emulsion, but it may also be incorporated in a non-sensitized emulsion or an emulsion layer having light sensitivity in the three primary colors region of spectrum except for red.

Each constituent unit for forming a dye image in the present invention comprises a single emulsion layer or a multi-layer emulsion layer having a light sensitivity to a certain region of spectrum.

Including the layer for image forming unit as mentioned above, the layers necessary for the light-sensitive silver halide color photographic materials can be arranged in various orders as known in this field of the art. A typical multi-color light-sensitive silver halide color photographic material comprises a cyan dye image forming constituent unit comprising at least one red-sensitive silver halide emulsion layer having at least one cyan dye forming coupler (at least one of the cyan dye forming couplers being the cyan coupler of the present invention), a magenta dye image forming constituent unit comprising at least one green-sensitive silver halide emulsion layer having at least one magenta dye forming coupler and a yellow dye image forming constituent unit comprising at least one blue-sensitive silver halide emulsion having at least one yellow dye forming coupler, all of the above image forming constituent unit being carried on a support.

The light-sensitive photographic material can also have additional layers such as filter layer, intermediate layer, subbing layer, etc.

For preparation of a light-sensitive silver halide color photographic material by use of the couplers of the present invention, respective light-sensitive layers containing a yellow dye forming coupler and a magenta dye forming coupler, respectively, are further required.

The yellow dye forming couplers available may include those known in the art. For example, it is possible to use such compounds as shown by Formula [IV] shown below:

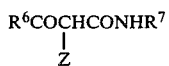  Formula [IV]

wherein $R^6$ represents an alkyl group or an aryl group, $R^7$ an aryl group and Z a hydrogen atom or an eliminable group through coupling reaction with the oxidized product of a color developing agent.

As the group Z in the formula [IV], Formulae [V] and [VI] shown below are preferred.

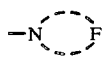  Formula [V]

wherein F represents a non-metallic atomic group capable of forming a 5- or 6-membered ring.

  Formula [VI]

wherein $R^8$ represents an aryl group, preferably a substituted phenyl group.

The magenta dye forming couplers available may include those known in the art. For example, such compounds as shown by the following Formula [VII], [VIII] and [IX] may be employed.

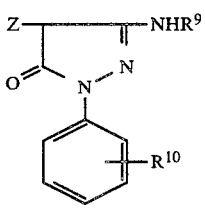  Formula [VII]

wherein $R^9$ represents an alkylcarbonyl group, an arylcarbonyl group or an aryl group, $R^{10}$ a monovalent group and Z a hydrogen atom or an eliminable group through coupling reaction with the oxidized product of a color developing agent.

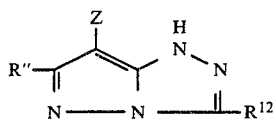  Formula [VIII]

wherein $R^{11}$ represents an alkyl group or an aryl group, $R^{12}$ an alkyl group, an aryl group or an alkylthio group and Z an eliminable group through coupling reaction with the oxidized product of a color developing agent.

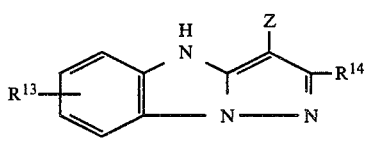  Formula [IX]

wherein $R^{13}$ represents a monovalent group, $R^{14}$ an alkyl group, an aryl group, an acylamino group or an alkoxy group and Z a hydrogen atom or an eliminable group through coupling reaction with the oxidized product of a color developing agent.

The cyan dye forming coupler of the present invention can be further combined with other cyan dye forming couplers.

Available cyan dye forming couplers may include those known in the art. For example, such compounds as shown by the following Formula [X] can be used.

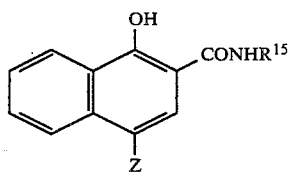  Formula [X]

wherein $R^{15}$ represents an alkyl group or an aryl group and Z a hydrogen atom or an eliminable group through coupling reaction with the oxidized product of a color developing agent.

The respective yellow, magenta and cyan couplers represented by the above Formulae [IV], [VII], [VIII], [IX], [X] may be exemplified by specific compounds as shown below, which are not limitative of the present invention. These respective couplers may be selected as desired and two or more compounds may also be used in combination.

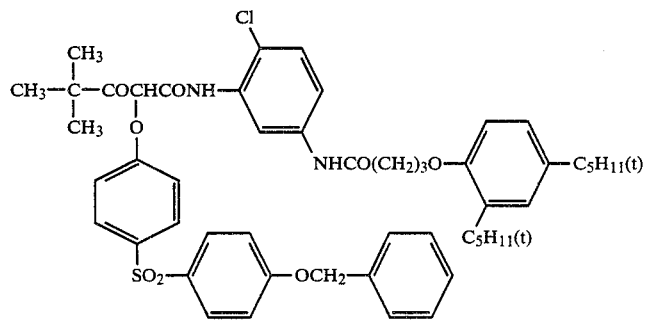

(Y-1)

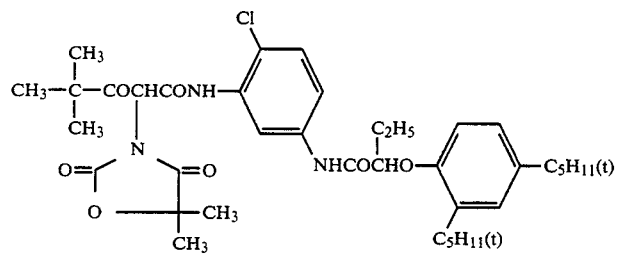
(Y-2)
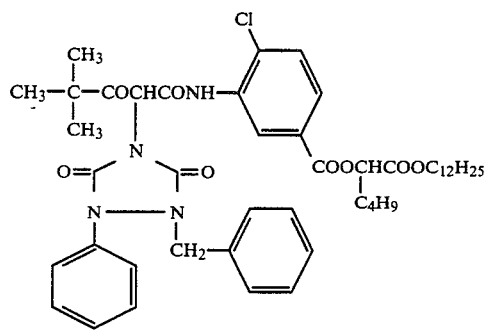
(Y-3)
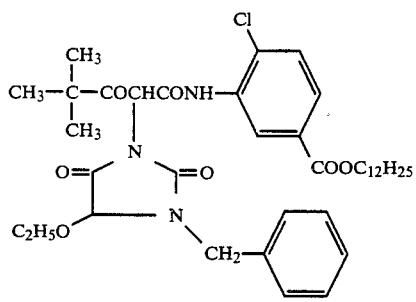
(Y-4)
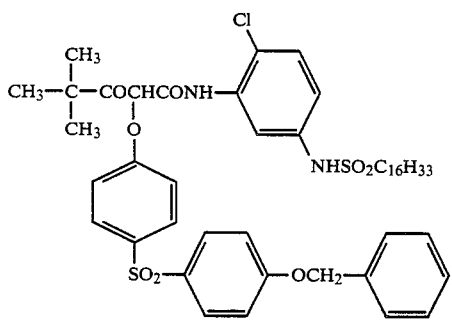
(Y-5)
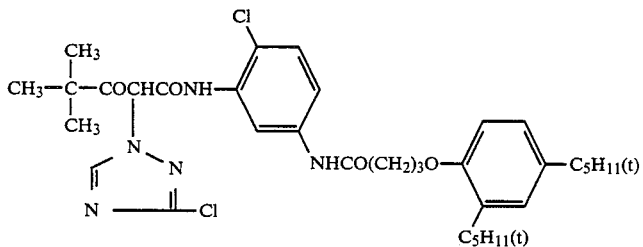
(Y-6)

-continued
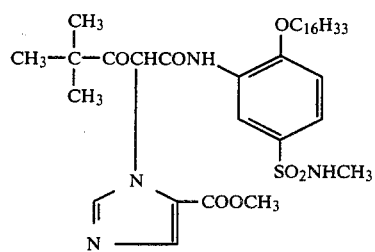 (Y-7)
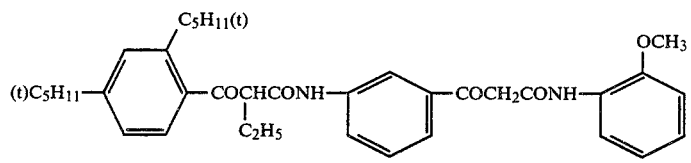 (Y-8)
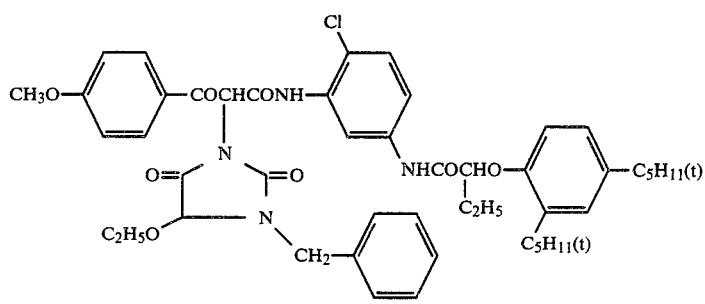 (Y-9)
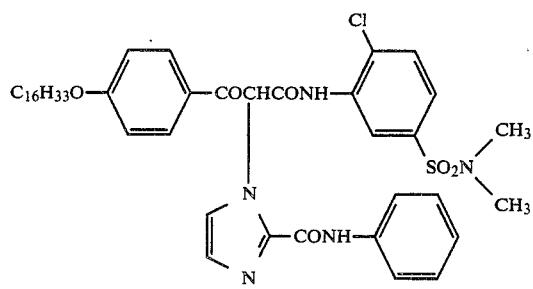 (Y-10)
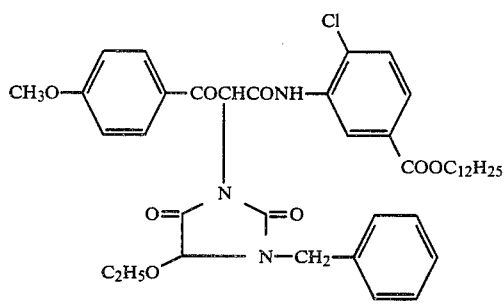 (Y-11)
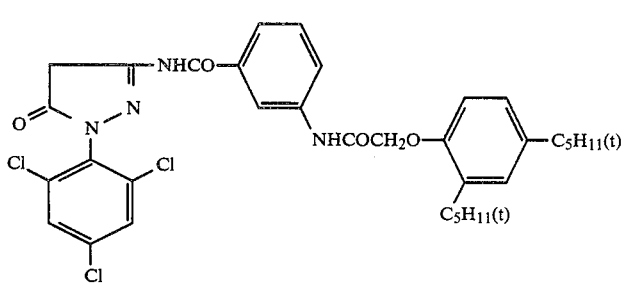 (M-1)

-continued
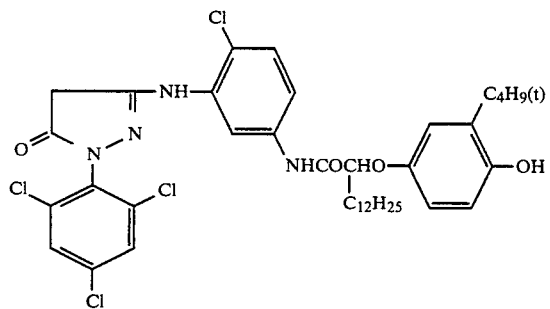
(M-2)
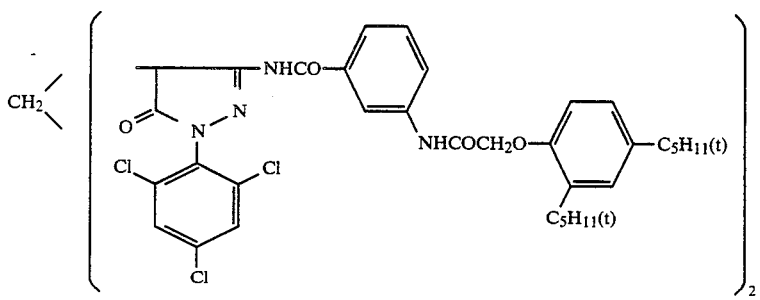
(M-3)
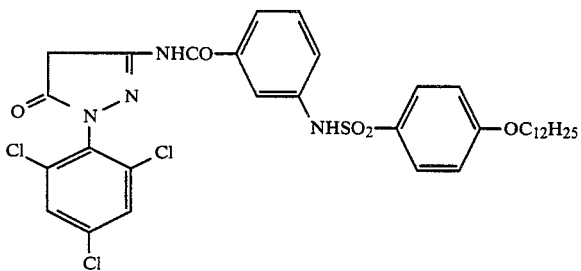
(M-4)
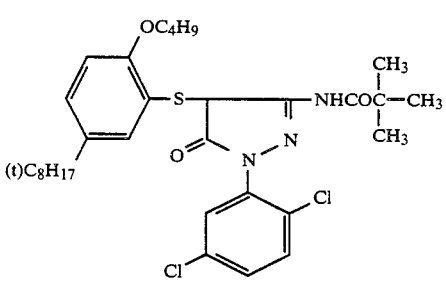
(M-5)
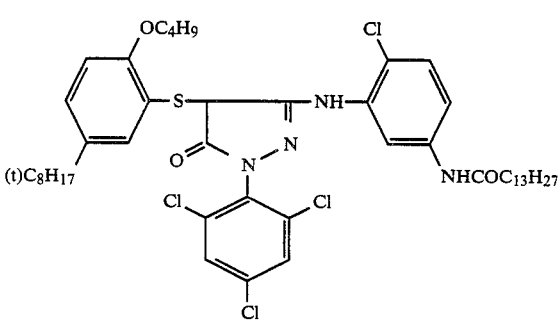
(M-6)

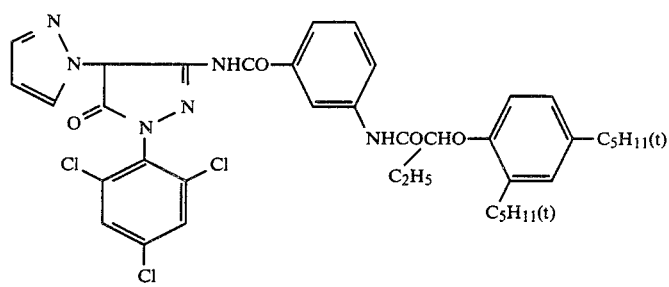
(M-7)
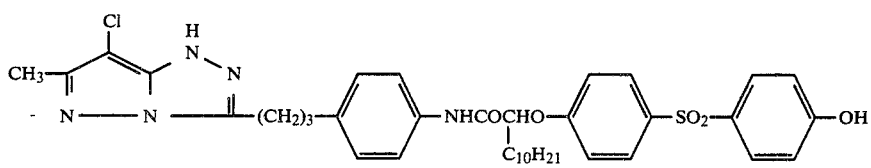
(M-8)
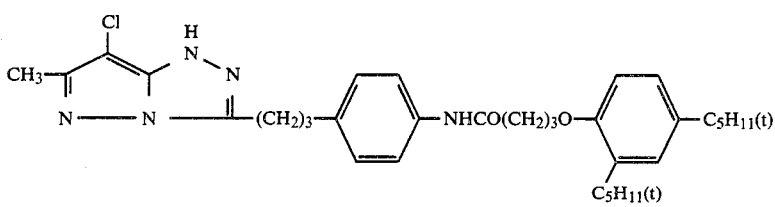
(M-9)
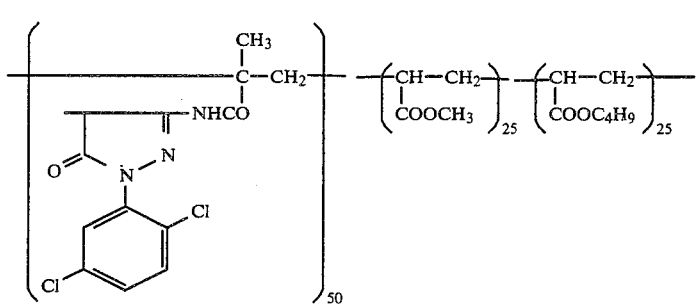
(M-10)
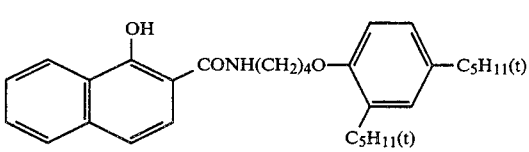
(C-1)
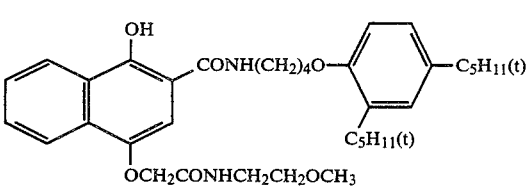
(C-2)
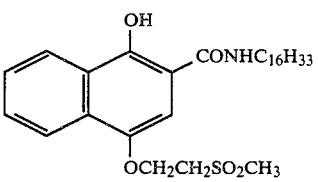
(C-3)

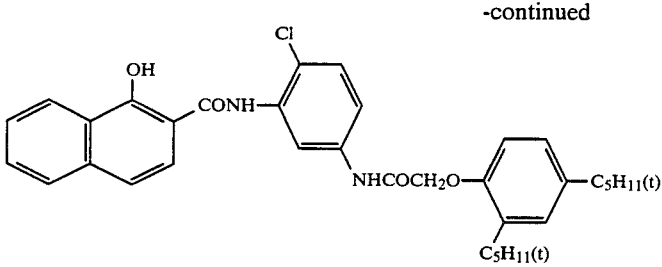
(C-4)

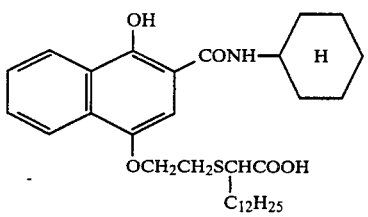
(C-5)

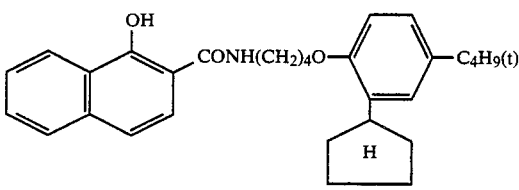
(C-6)

For incorporating the cyan coupler of the present invention and the respective couplers according to the present invention in a light-sensitive silver halide material, conventional methods known in the art may be employed. For example, after dissolving the cyan coupler or the respective couplers according to the present invention in a mixture of a known high boiling solvent and a low boiling solvent such as butyl acetate, butyl propionate, etc., the resultant solution is mixed with an aqueous gelatin solution containing a surfactant, then emulsified by a high speed rotary mixer, a colloid mill or a ultrasonic dispersing machine and thereafter the emulsion is added to silver halide to prepare the silver halide emulsion to be used in the present invention.

As the available high boiling solvent, there may be included those known in the art. For example, such compounds as represented by the following Formulae [XI], [XII], [XIII], [XIV] and [XV] may be employed. Among them, the compounds of Formulae [XI] and [XII] are preferable, and a diester of phthalic acid is particularly preferred.

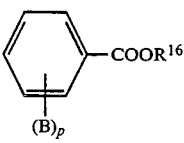
Formula [XI]

wherein B represents a halogen atom, an alkoxy group having 1 to 20 carbon atoms or —COOR$^{16}$, R$^{16}$ an alkyl group having 1 to 20 carbon atoms or a phenyl group, p an integer of 0 to 3; when p is 2 or more, the plural groups represented by B may be either identical or different.

O=P(—OR$^{16}$)$_3$   Formula [XII]

wherein R$^{16}$ is the same as defined in the above Formula [XI].

$$R^{17}CON\begin{smallmatrix}R^{18}\\R^{19}\end{smallmatrix}$$   Formula [XIII]

wherein R$^{17}$ and R$^{18}$ each represent an alkyl group having 1 to 20 carbon atoms or a phenyl group, R$^{19}$ a hydrogen atom or an alkyl group having 1 to 20 carbon atoms or a phenyl group; and R$^{18}$ and R$^{19}$ may form a 5- to 6-membered ring by use of a non-metallic atomic group.

R$^{20}$COOR$^{16}$   Formula [XIV]

wherein R$^{20}$ represents an alkyl group having 1 to 20 carbon atoms and R$^{16}$ is the same as defined in the above Formula [XI].

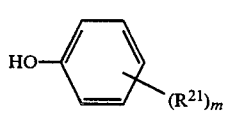
Formula [XV]

wherein R$^{21}$ represents an alkyl group having 1 to 20 carbon atoms, m an integer of 1 to 3; when m is 2 or more, the plural groups represented by R$^{21}$ may be either identical or different.

The high boiling solvents represented by the above Formulae [XI], [XII], [XIII], [XIV] and [XV] may be exemplified by the compounds as enumerated below, which are not limitative of the present invention. These high boiling solvents may be selected as desired, and two or more compounds may be used in combination.

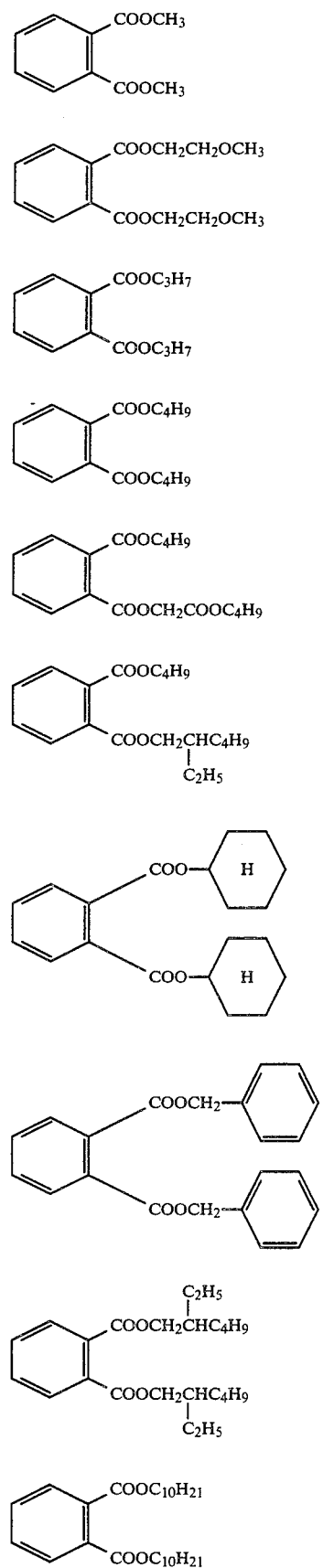
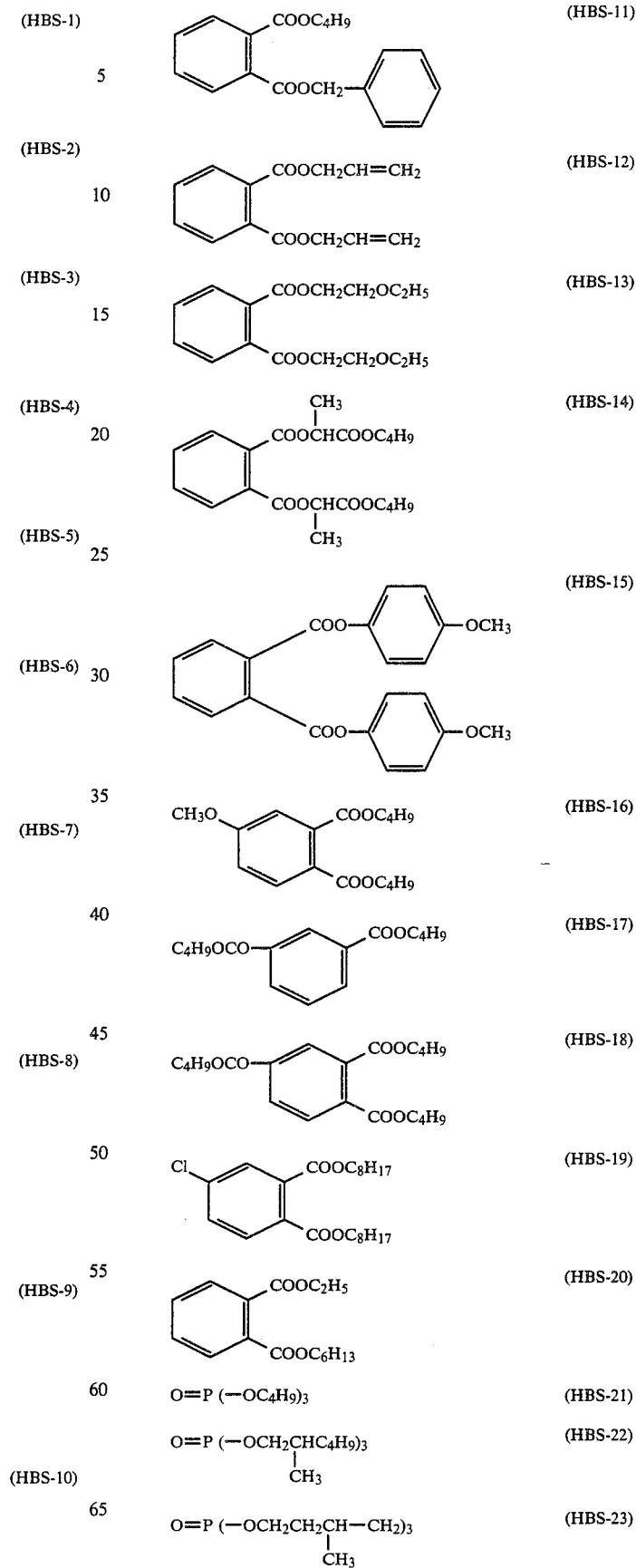

O=P(—OC₆H₁₃)₃  (HBS-24)
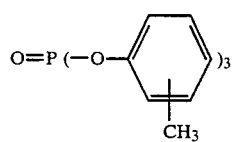 (HBS-25)
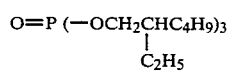 (HBS-26)
O=P(—OCH₂CHC₄H₉)₃
          |
          C₂H₅  (HBS-27)
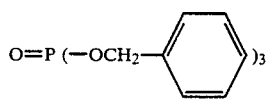 (HBS-28)
O=P(—OCH₂—⌬)₃  (HBS-29)
         C₂H₅
         |
O=P(—OCH₂CHC₄H₉)₂
    |
    OC₄H₉   (HBS-30)
O=P(—OCH₂CH₂CHCH—CH₃)₃
                |   |
                CH₃ CH₃  (HBS-31)
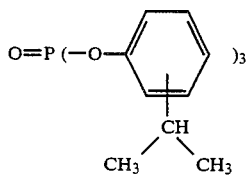 (HBS-32)
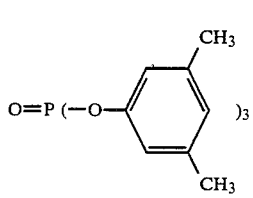 (HBS-33)
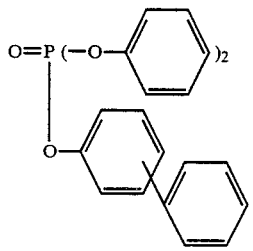 (HBS-34)
O=P(—OC₈H₁₇)₂
    |
    OCH₂—⌬   (HBS-35)
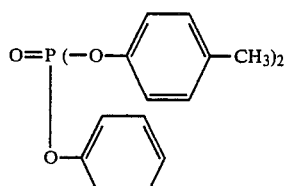 (HBS-36)
         C₂H₅
         |
C₁₁H₂₃CON
         |
         C₂H₅   (HBS-37)
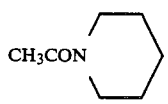 (HBS-38)
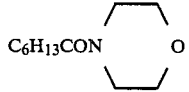 (HBS-39)
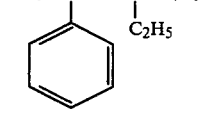 (HBS-40)
CH₃CONCH₂CH₂COOC₄H₉
     |
     C₆H₁₃   (HBS-41)
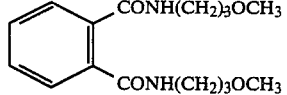 (HBS-42)
CH₃COOC₁₂H₂₅  (HBS-43)
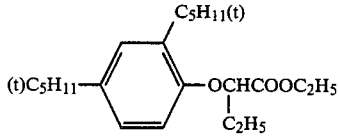 (HBS-44)
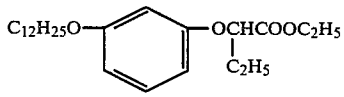 (HBS-45)
C₁₁H₂₃COOC₂H₅  (HBS-46)
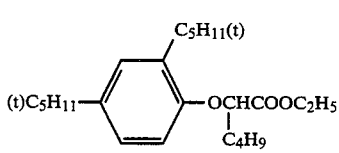 (HBS-47)
C₂H₅
    \
     CHCOOCH₂—⌬
    /
C₄H₉   (HBS-48)
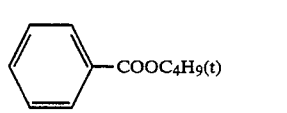 (HBS-49)

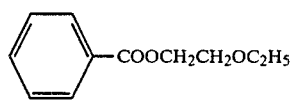 (HBS-50)

CH₃COOCH₂CH₂OCH₂CH₂OC₄H₉ (HBS-51)

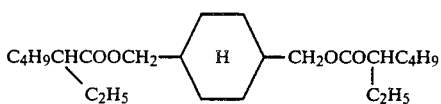 (HBS-52)

CH₃CONC₄H₉
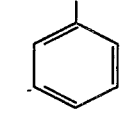

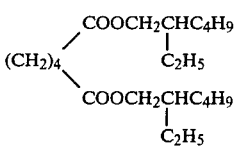 (HBS-54)

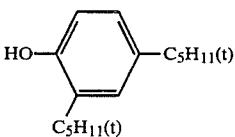 (HBS-55)

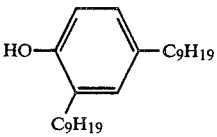 (HBS-56)

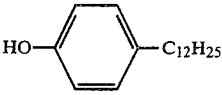 (HBS-57)

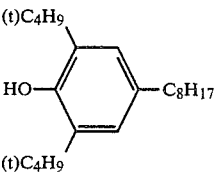 (HBS-58)

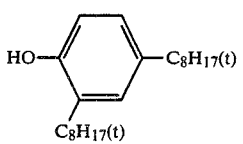 (HBS-59)

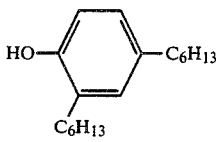 (HBS-60)

In the light-sensitive silver halide color photographic material prepared by the present invention, it is also possible to incorporate a colored coupler for color correction, a so-called DIR coupler, a non-coloration coupler for hue improvement of the light-sensitive material or various additives conventionally used such as UV-ray absorbers, stabilizers of photographic performance, etc.

Available colored couplers may include colored magenta couplers and colored cyan couplers, as represented by the following Formulae [XVI] and [XVII].

$$M-N=N-Ar \qquad \text{Formula [XVI]}$$

wherein M represents a residue of a magenta coupler from which a hydrogen atom at the active site is removed, and Ar and aryl group.

$$C-(J)_q-N=N-Ar \qquad \text{Formula [XVII]}$$

wherein C represents a residue of a phenol type or naphthol type cyan coupler from which hydrogen is removed at the active site, J a divalent linking group, Ar an aryl group, and q is 0 or 1.

The M in Formula [XVI] may preferably a magenta coupler as represented by the above Formula [VII] ($R^9$ is a substituted phenyl group). On the other hand, the C in Formula [XVII] may preferably a cyan coupler represented by the above Formula [X], and q preferably 1.

The colored magenta couplers and the colored cyan couplers represented by Formulae [XVI] and [XVII] may include the compounds an enumerated below, which are not limitative of the present invention, and two or more compounds may be used in combination.

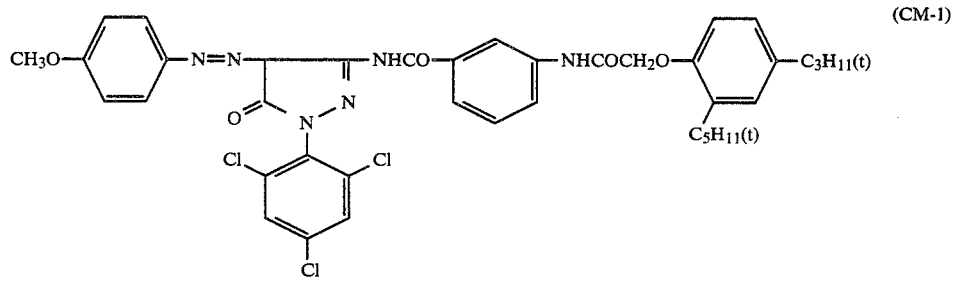 (CM-1)

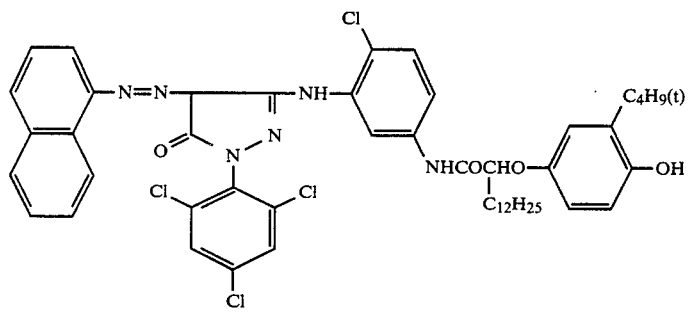
(CM-2)
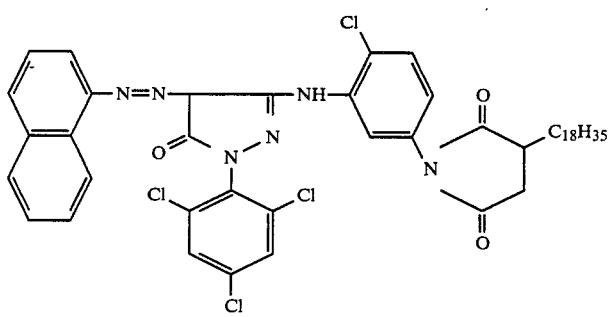
(CM-3)
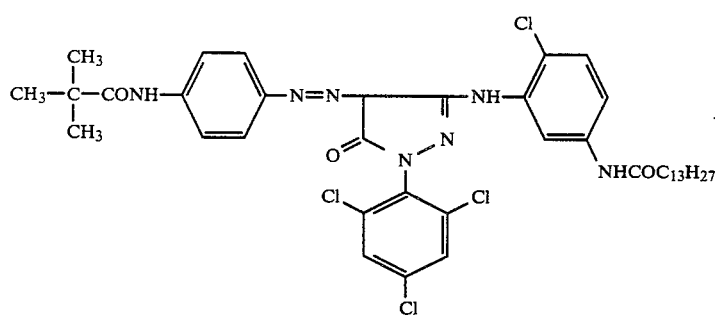
(CM-4)
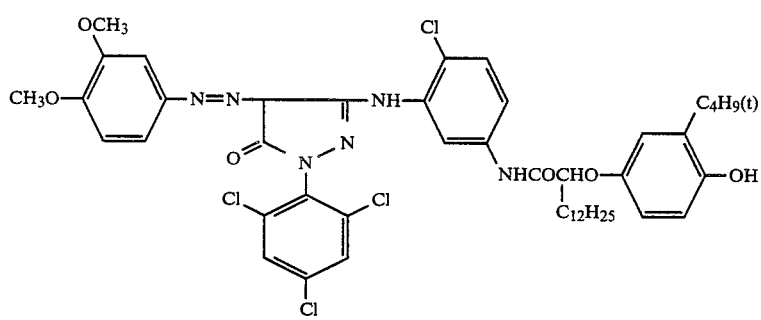
(CM-5)
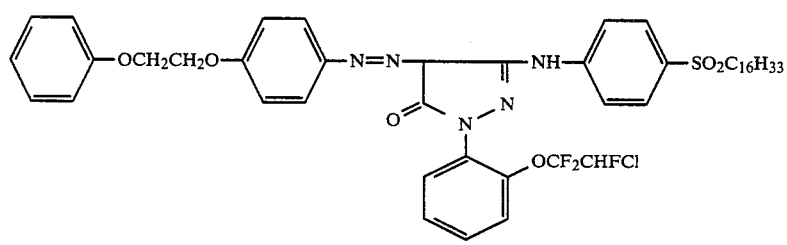
(CM-6)

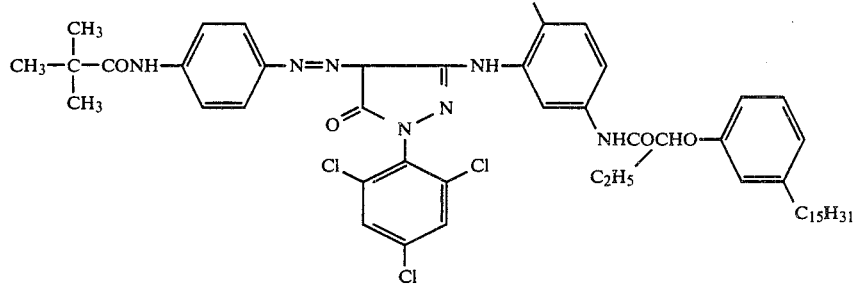
(CM-7)
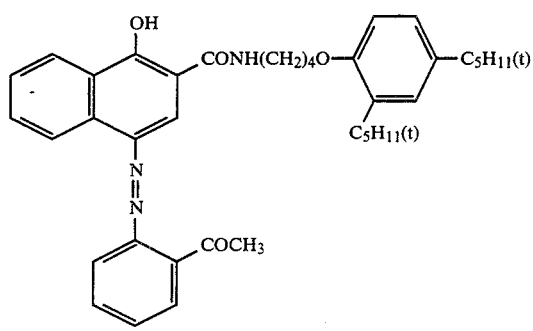
(CC-1)
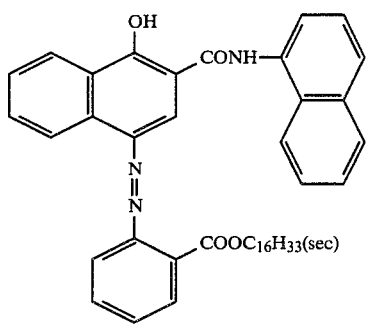
(CC-2)
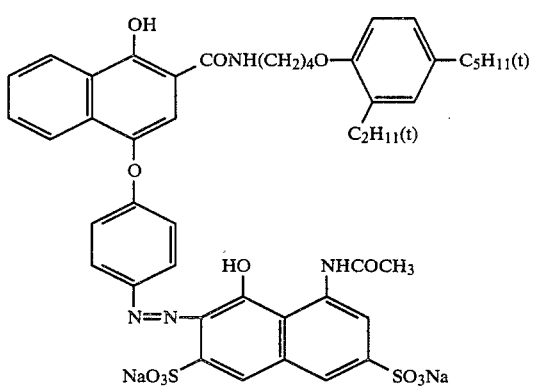
(CC-3)
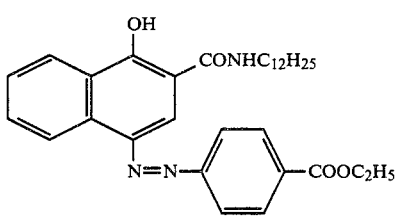
(CC-4)

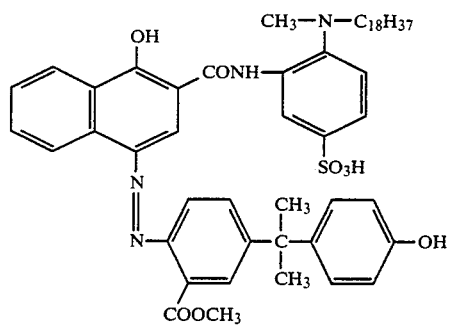

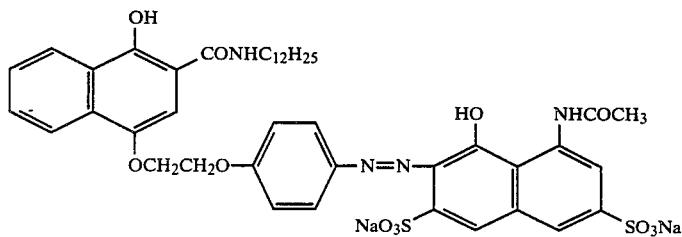

Available DIR couplers may be represented by the following Formula [XVIII]:

$$Cp-(J')_q-I \qquad \text{Formula [XVIII]}$$

wherein Cp represents a residue of a group having a site capable of coupling with the oxidized product of a color developing agent, from which a hydrogen atom is removed, J' a divalent group which is released from Cp through the reaction with the oxidized product of a color developing agent and can release I by intramolecular nucleophilic substitution reaction, electron transfer or hydrolysis, I a developing inhibiting group and q is 0 or 1.

Preferable DIR couplers are shown below, but they are not limitative of the present invention, and the respective couplers can be selected variously depending on the objects and uses, and two or more couplers may be used in combination, if desired.

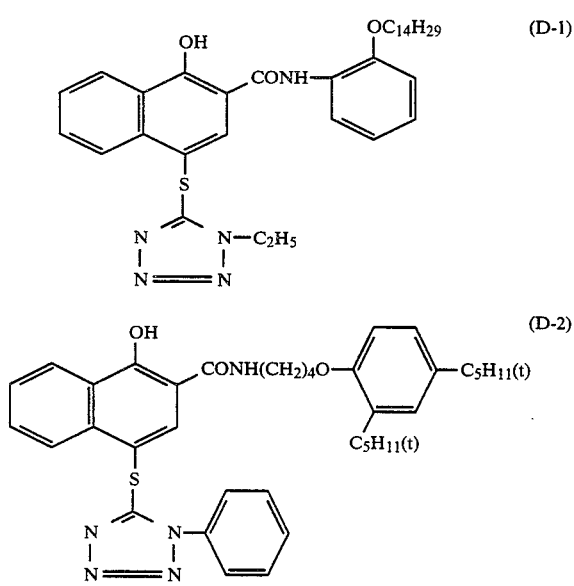

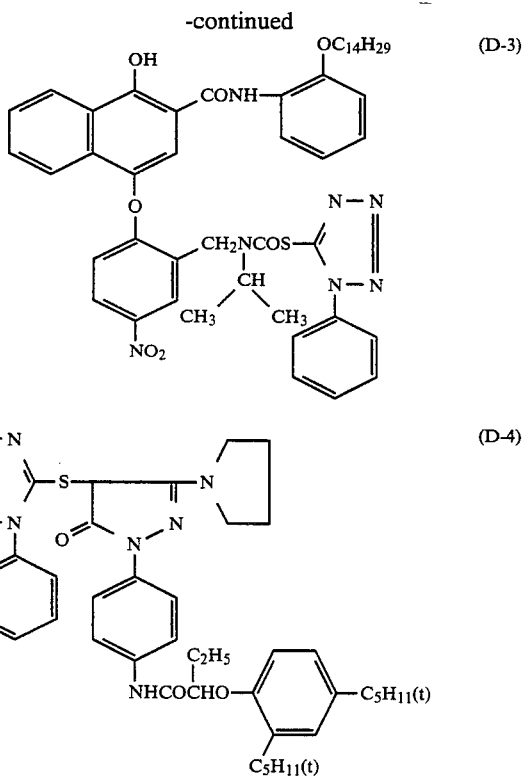

-continued
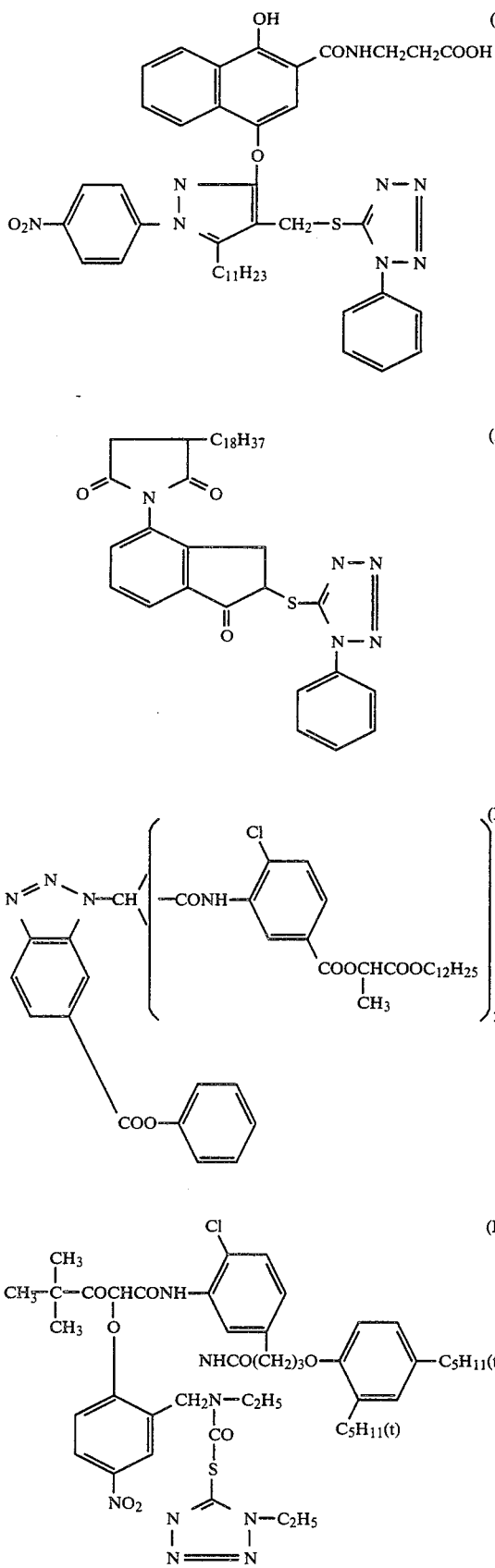
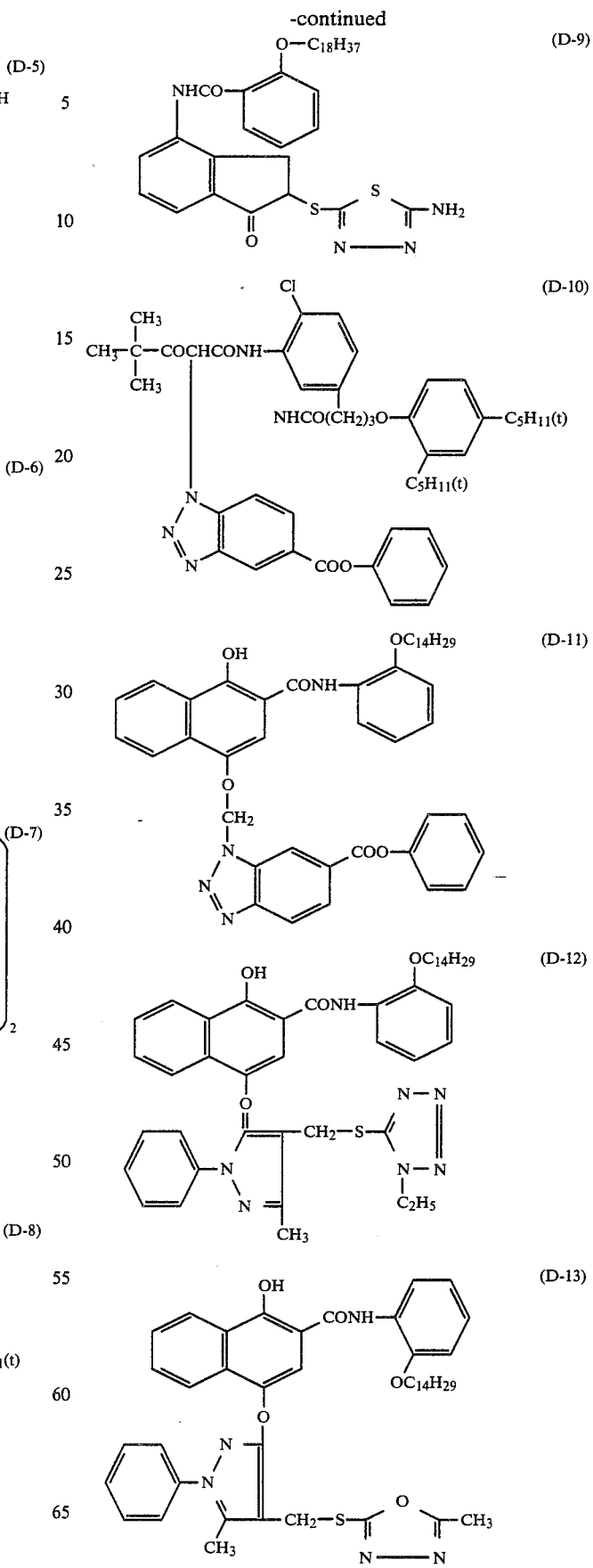

UV-ray absorbers available in the present invention may be represented by the following Formula [XIX] and [XX].

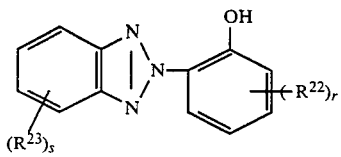

Formula [XIX]

wherein $R^{22}$ represents an alkyl group having 1 to 20 carbon atoms, $R^{23}$ a halogen atom, r an integer of 1 or 2 and s an integer of 0 or 1; when r is 2, the two groups represented by $R^{22}$ may be either identical or different.

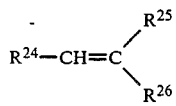

Formula [XX]

wherein $R^{24}$ represents an aryl group or a vinyl group, $R^{25}$ and $R^{26}$ each represent a cyano group, an alkoxycarbonyl group or an arylsulfonyl group.

In the following, specific examples of UV-absorbers are set forth, but they are not limitative of the present invention. If desired, two or more compounds may be used in combination.

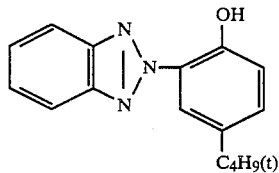 (U-1)

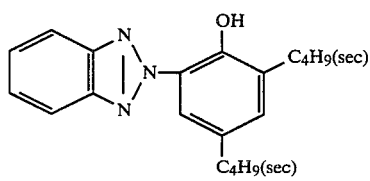 (U-2)

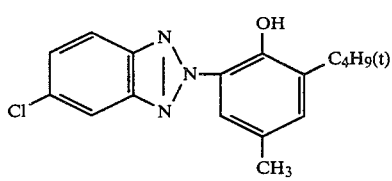 (U-3)

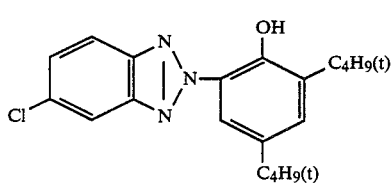 (U-4)

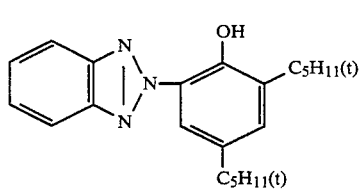 (U-5)

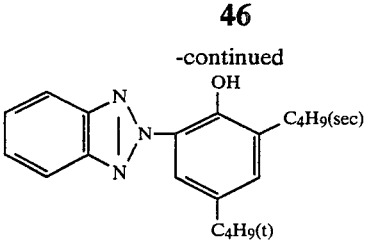 (U-6)

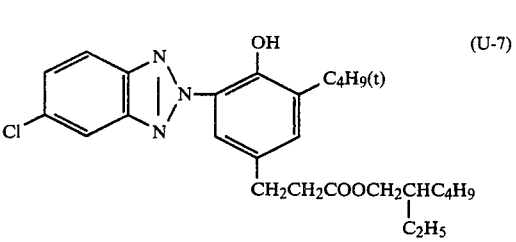 (U-7)

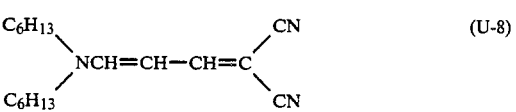 (U-8)

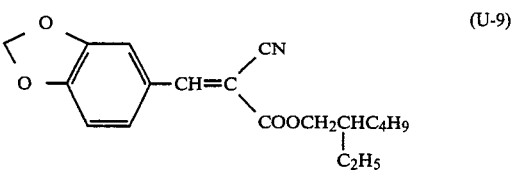 (U-9)

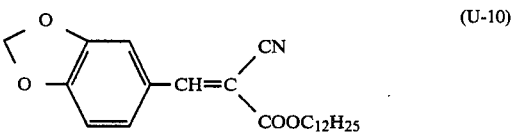 (U-10)

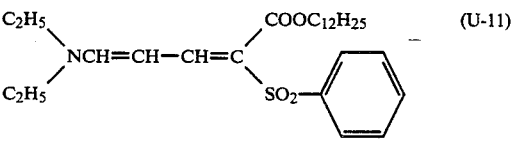 (U-11)

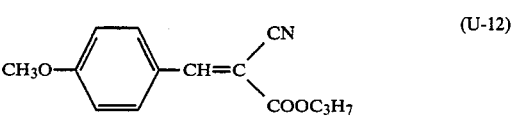 (U-12)

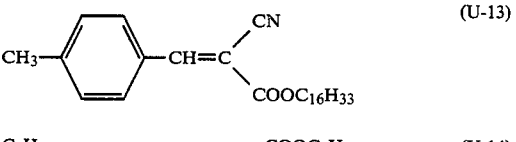 (U-13)

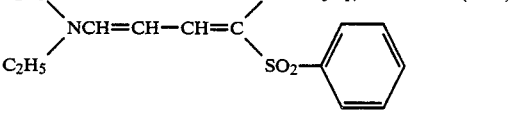 (U-14)

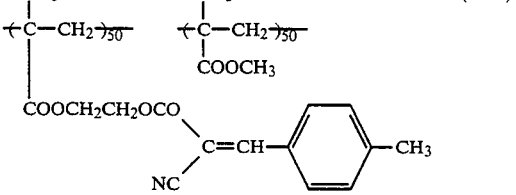 (U-15)

Available stabilizers may include antifoggants, image dye stabilizers, as represented by the following Formulae [XXI], [XXII], [XXIII].

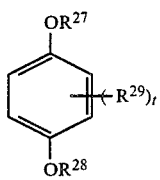

Formula [XXI]

wherein $R^{27}$ and $R^{28}$ each represent a hydrogen atom or an alkyl group having 1 to 20 carbon atoms, $R^{29}$ an alkyl group having 1 to 20 carbon atoms or a sulfoxy group and t an integer of 1 or 2; when t is 2, the two groups represented by $R^{29}$ may be either identical or different; or $R^{28}$ and $R^{29}$ may form a 5- or 6-membered ring by use of a non-metallic atomic group.

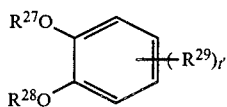

Formula [XXII]

wherein $R^{27}$, $R^{28}$ and $R^{29}$ are the same as defined in the above formula [XXI] and t' represents an integer of 1 or 2; when t' is 2, the two groups represented by $R^{29}$ may be either identical or different; or $R^{29}$ may form a 5- or 6-membered ring at the ortho position.

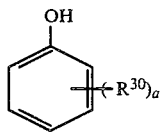

Formula [XXIII]

wherein $R^{30}$ is an alkyl group having 1 to 20 carbon atoms, a phenoxycarbonyl group, a benzenesulfonamide group or an alkylsulfonamide group, a an integer of 1 to 3; when a is 2 or more, the plural groups represented by $R^{30}$ may be either identical or different.

Examples of stabilizers represented by the Formulae [XXI], [XXII] and [XXIII] are shown below, but they are not limitative of the present invention. If desired, two or more compounds may be used in combination.

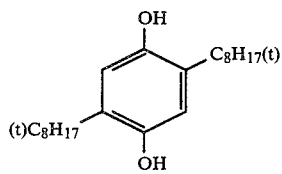

(A-1)

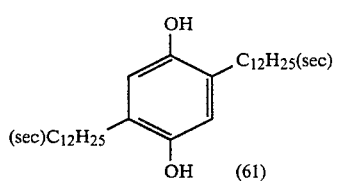

(A-2) (61)

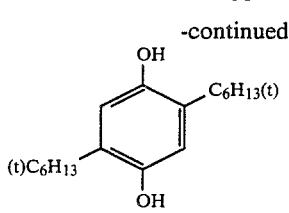

(A-3)

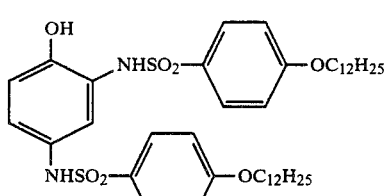

(A-4)

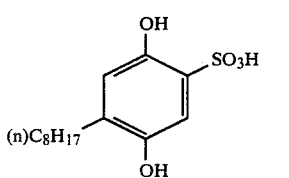

(A-5)

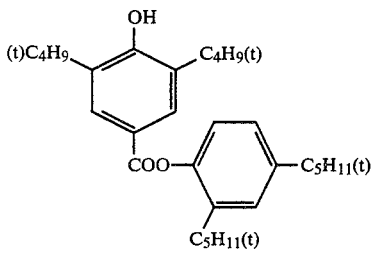

(A-6)

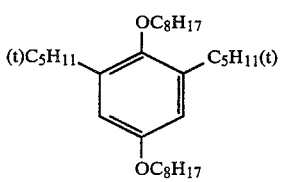

(A-7)

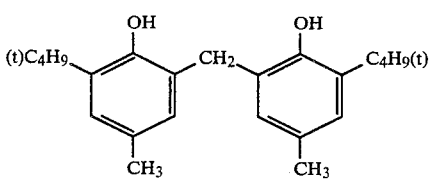

(A-8)

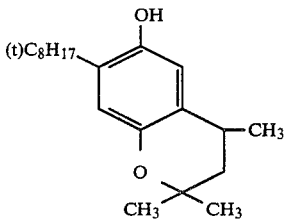

(A-9)

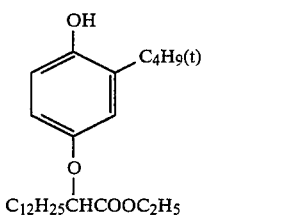

(A-10)

-continued

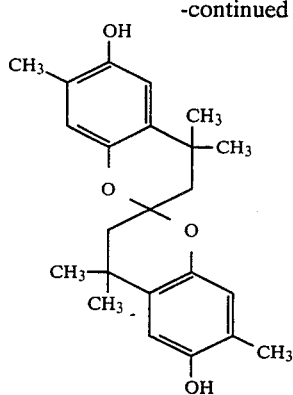
(A-11)

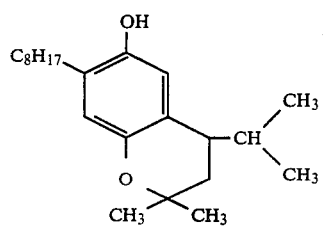
(A-12)

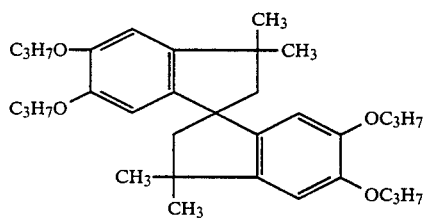
(A-13)

When the cyan coupler of the present invention and the respective couplers according to the present invention are to be added into the silver halide emulsion, each may be added generally in an amount of about 0.005 to 2 mole, preferably 0.01 to 0.5 mole per mole of the silver halide.

The silver halide to be used in the silver halide emulsion of the present invention may include any of those conventionally used in silver halide emulsions such as silver bromide, silver chloride, silver iodobromide, silver chlorobromide, silver chloroiodobromide, etc.

The silver halide emulsion constituting the silver halide emulsion layer according to the present invention can be prepared according to various methods including all conventional preparations methods, such as the method as disclosed in Japanese Patent Publication No. 7772/1971, namely the method for preparation of the so-called conversion emulsion in which an emulsion of silver salt grains comprising at least a part of silver salts with greater solubility than silver bromide is formed, and subsequently at least a part of the grains are converted to silver bromide or silver iodobromide, or the method for preparation of Lipman emulsion comprising microparticulate silver halide having a mean grain size of 0.1 μm or less. Further, the silver halide emulsion of the present invention can be sensitized chemically with a sulfur sensitizer such as arylthiocarbamide, thiourea, cystine, etc., or an active or inactive selenium sensitizer, and a reductive sensitizer such as a stannous salt, a polyamine, etc., a noble metal sensitizer, such as gold sensitizers, typically potassium aurithiocyanate, potassium chloroaurate, 2-aurosulfobenzthiazolmethyl chloride, etc. or sensitizers of water soluble salts of ruthenium, rhodium, iridium, etc., typically ammonium chloropalladate, potassium chloroplatinate and sodium chloropalladite, etc., which can be used either singly or in a suitable combination.

Also, the silver halide emulsion to be used in the present invention can incorporate various known additives for photography, as disclosed in, for example, "Research Disclosure", No. 17643, December, 1978.

The silver halide to be used in the present invention may be subjected to spectral sensitization by choice of an appropriate sensitizing dye, in order to impart light-sensitivity to the necessary light-sensitive wavelength region. Various kinds of such spectral sensitizing dyes are available, and one or a combination of two or more of these dyes can be used.

As the spectral sensitizing dye advantageously used in the present invention, there may be included cyanine dyes, merocyanine dyes or complex cyanine dyes as disclosed in U.S. Pat. NOs. 2,269,234; 2,270,378; 2,442,710; 2,454,620; and 2,776,280 as representative ones.

The above-mentioned support according to the present invention may be any of plastic films, plastic laminate papers, baryta papers, synthetic papers, etc. known in the art, which may be selected suitably depending on the intended use of the light-sensitive photographic material. These supports may generally be applied with subbing treatment for reinforcement of adhesion to the photographic emulsion layer.

For the light-sensitive silver halide color photographic material thus constituted, various photographic processing methods may be employed as the color developing process after exposure. The preferable color developer to be used in the present invention contains an aromatic primary amine type color developing agent as a main component. Typical examples of such a color developing agent are p-phenylenediamine type agents, including diethyl-p-phenylenediamine hydrochloride, monomethyl-p-phenylene-diamine hydrochloride, dimethyl-p-phenylenediamine hydrochloride, 2-amino-5-diethylaminotoluene hydrochloride, 2-amino-5-(N-ethyl-N-β-hydroxylethyl-amino)toluene, 2-amino-5-(N-ethyl-N-β-methanesulfonamido-ethyl)aminotoluene sulfate, 2-amino-5-(N-ethyl-N-β-methanesulfonamidoethylamino)toluene, 4-(N-ethyl-N-β-hydroxyethylamino)aniline, 2-amino-5-(N-ethyl-β-methoxyethyl)aminotoluene and the like. Among them, the color developing agent to be used particularly preferably during processing of the light-sensitive photographic material of the present invention may be selected from 2-amino-5-(N-ethyl-N-β-hydroxyethylamino)toluene and 2-amino-5-(N-ethyl-N-β-methanesulfonamidoethylamino)toluene. These color developing agents may be used either singly or as a combination of two or more kinds, or in combination with a black-and-white developing agent, for example, hydroquinone, if desired. Further, the color developer may also contain an alkali agent such as sodium hydroxide, ammonium hydroxide, sodium carbonate, sodium sulfite, etc., and further various additives such as alkali metal halides (e.g. potassium bromide) or developing controllers such as citrazinic acid, etc.

The light-sensitive silver halide color photographic material of the present invention may contain the above color developing agent as the color developing agent itself, or alternatively as its precursor in a hydrophilic colloid layer. A color developing agent precursor is a compound capable of forming a color developing agent under alkaline conditions, including Schiff base type precursor with an aromatic aldehyde derivative, polyvalent metal ion complex precursor, phthalic imide derivative precursor, phosphoric amide derivative precursor, sugar-amine reaction product precursor, urethane type precursor, etc. The precursors of these aromatic primary amine type color developing agents are disclosed in U.S. Pat. Nos. 3,342,599; 2,507,114; 2,695,234; 3,719,492; U.K. Pat. No. 803,783; Japanese Unexamined Patent Publications Nos. 135628/1978, 79035/1979, Research Disclosure Nos. 15,159, 12,146 and 13,924.

These aromatic primary amine type color developing agents or precursors thereof are required to be added in amounts sufficient to give satisfactory color formation during developing processing. The amount may vary significantly depending on the kind of the light-sensitive material, but generally between 0.1 mole and 5 moles, preferably between 0.5 mole and 3 moles, per mole of the light-sensitive silver halide. These color developing agents or precursors thereof may be used either singly or in combination. In order to have the above compounds included in a light-sensitive photographic material, they can be added as a solution dissolved in a suitable solvent such as water, methaol, ethanol, acetone, etc., or as an emulsion employing a high boiling organic solvent such as dibutyl phthalate, dioctyl phthalate, tricresyl phosphate, etc., or also incorporated by impregnation into a latex polymer as disclosed in Research Disclosure No. 14850.

The light-sensitive silver halide color photographic material of the present invention is oridinarily subjected to respective processings of bleaching and fixing or bleach-fixing and washing with water, after color developing processing. As the bleaching agent, a number of compounds may be used. Among them, polyvalent metal compounds such as of iron (III), cobalt (III), tin (II), etc., and above all complexes of these polyvalent metal cations with organic acids, for example, metal complexes of aminopolycarboxylic acids such as ethylenediaminetetraacetic acid, nitrilotriacetic acid, N-hydroxyethylenediamine diacetic acid, or metal complexes of malonic acid, tartaric acid, malic acid, diglycolic acid, thioglycolic acid, etc. or ferricyanates, bichromates, etc. may be used either singly or in a suitable combination.

The present invention is described in more detail by referring to the following Examples, by which the present invention is not limited.

EXAMPLE 1

As shown in Table 1, each 0.1 mole of the cyan couplers of the present invention was weighed per one mole of silver, and dibutyl phthalate (as high boiling solvent) as the coupler and ethyl acetate were added there to, in an amount equivalent to and 3-fold of the amount of the coupler, respectively, and the coupler was completely dissolved in these solvents by heating to 60° C. Also, for comparison, each 0.1 mole of Control couplers known in the art was weighed per 1 mole of silver, and dibutyl phthalate as the coupler and ethyl acetate were added thereto, in an amount equivalent to and 3-fold of the amount of the Control coupler, respectively, and the coupler was completely dissolved in these solvents by heating to 60° C. The solution was mixed with 1200 ml of an aqueous 5% gelatin solution containing 120 ml of an aqueous 5% solution of Alkanol B (alkylnaphthalene sulfonate: produced by Du Pont Co.), dispersed by means of a ultrasonic dispersing machine to obtain an emulsion. Then, the dispersion was added to 4 kg of a red-sensitive silver iodobromide emulsion (containing 7 mole % of silver iodide), followed by addition of 120 ml of a 2% solution of 1,2-bis(-vinylsulfonyl)ethane (water:methanol=1:1) as film hardener, and the resultant mixture was applied on a transparent polyester base subjected to subbing treatment and dried to give a sample having a stable coated film (coated silver quantity: 15 mg/100 cm$^2$).

The sample thus obtained was subjected to wedge exposure in a conventional manner, and the following developing processing was performed. The results are shown in Table 1.

Sensitivity and the maximum color forming density were measured by PDA-65 Model Densitometer produced by Konishiroku Photo Industry Co., Ltd.

| [Processing step] (38° C.) | Processing time |
| --- | --- |
| Color developing | 3 min. 15 sec. |
| Bleaching | 1 min. 30 sec. |
| Water washing | 3 min. 15 sec. |
| Fixing | 6 min. 30 sec. |
| Water washing | 3 min. 15 sec. |
| Stabilizing bath | 1 min. 30 sec. |

The processing liquors employed in the processing steps had the compositions as shown below.

| [Color developing solution] | |
| --- | --- |
| 4-Amino-3-methyl-N—ethyl-N—(β-hydroxyethyl)-aniline sulfate | 4.75 g |
| Anhydrous sodium sulfite | 4.25 g |
| Hydroxyamine ½ sulfate | 2.0 g |
| Anhydrous potassium carbonate | 37.5 g |
| Sodium bromide | 1.3 g |
| Trisodium nitrilotriacetate (monohydrate) | 2.5 g |
| Potassium hydroxide | 1.0 g |
| (made up to one liter with water and adjusted to pH 10.0 with potassium hydroxide) | |
| [Bleaching solution] | |
| Ferric ammonium ethylenediaminetetraacetate | 100.0 g |
| Diammonium ethylenediaminetetraacetate | 10.0 g |
| Ammonium bromide | 150.0 g |
| Glacial acetic acid | 10.0 ml |
| (made up to one liter with water and adjusted to pH 6.0 with aqueous ammonia) | |
| [Fixing solution] | |
| Ammonium thiosulfate (50% aqueous solution) | 162 ml |
| Anhydrous sodium sulfite | 12.4 g |
| (made up to one liter with water and adjusted to pH 6.5 with acetic acid) | |
| [Stabilizing solution] | |
| Formalin (37% aqueous solution) | 5.0 ml |
| Konidax (produced by Konishiroku Photo Industry Co., Ltd.) | 7.5 ml |
| (made up to one liter with water) | |

TABLE 1

| Sample No. | Coupler No. | Relative sensitivity | Maximum color forming density | Maximum absorption wavelength | Δλs |
| --- | --- | --- | --- | --- | --- |
| 1 | C-1 | 100 | 1.95 | 696 | 123 |
| 2 | Control coupler(A) | 102 | 2.15 | 689 | 133 |
| 3 | Control coupler(B) | 114 | 2.24 | 688 | 132 |
| 4 | Control coupler(C) | 105 | 2.16 | 689 | 132 |
| 5 | Control coupler(D) | 102 | 2.20 | 689 | 135 |

TABLE 1-continued

| Sample No. | Coupler No. | Relative sensitivity | Maximum color forming density | Maximum absorption wavelength | Δλs |
|---|---|---|---|---|---|
| 6 | Control coupler(E) | 115 | 2.28 | 690 | 133 |
| 7 | Exemplary coupler(4) | 105 | 2.15 | 691 | 130 |
| 8 | Exemplary coupler(6) | 106 | 2.18 | 690 | 128 |
| 9 | Exemplary coupler(7) | 118 | 2.25 | 690 | 128 |
| 10 | Exemplary coupler(8) | 127 | 2.75 | 690 | 128 |
| 11 | Exemplary coupler(10) | 101 | 2.15 | 689 | 130 |

In the Table, relative sensitivities are represented relative to the sensitivity obtained in Sample No. 1 as 100, the maximum absorption wavelength ($\lambda_{max}$) is the wavelength in the spectral absorption curve at which a maximum density of 1.0 is exhibited, and $\Delta\lambda_s$ is exhibited as a value obtained by subtracting the absorption wavelength on the shorter wavelength side giving a density of 0.2 in the spectral absorption curve, from $\lambda_{max}$.

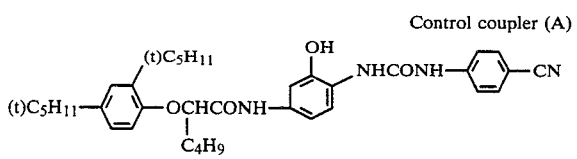

Control coupler (A)

(Compound as disclosed in Japanese Unexamined Patent Publication No. 65134/1981)

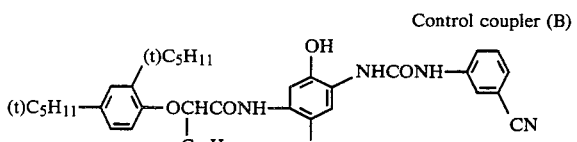

Control coupler (B)

(Compound as disclosed in Japanese Unexamined Patent Publication No. 204544/1982)

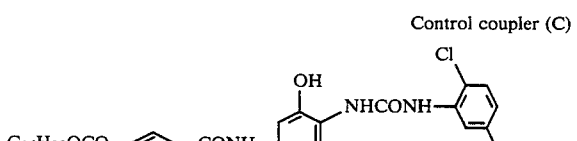

Control coupler (C)

(Compound as disclosed in Japanese Unexamined Patent Publication No. 204544/1982)

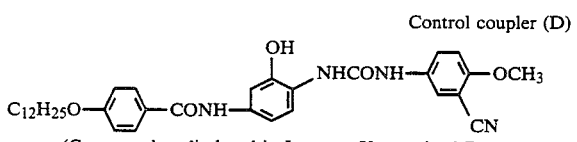

Control coupler (D)

(Compound as disclosed in Japanese Unexamined Patent Publication No. 204544/1982)

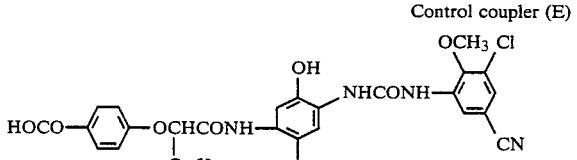

Control coupler (E)

(Compound as disclosed in Japanese Unexamined Patent Publication No. 204544/1982)

As is apparent from Table 1, all of the couplers of the present invention (Sample Nos. 7-11) exhibit sensitivities and maximum color forming densities which are equal to or better than those of Control couplers. As for the maximum absorption wavelength and $\Delta\lambda_s$, as compared with Control couplers (A)-(E), the maximum absorption wavelength approximately at least equal to those of Control couplers, while all of the samples were less in $\Delta\lambda_s$, thus giving favorable results in color reproduction. Particularly, the difference in these numerical values is a great significant difference when its effect extending to the region of green light is taken into consideration, whereby a great improvement effect could be brought about in view of color reproduction.

EXAMPLE 2

The samples obtained in Example 1 were subjected to wedge exposure and then applied with the developing processing of Example 1. On the other hand, processing with a bleach-fixing solution changed to have the following composition was performed, and fading of the cyan dye obtained by processing with a fatigued bleach-fixing solution was examined.

| [Bleach-fixing solution] | |
|---|---|
| Ferric ammonium ethylenediaminetetraacetate | 50 g |
| Ammonium sulfite (40% solution) | 50 ml |
| Ammonium thiosulfate (70% solution) | 140 ml |
| Aqueous ammonia (28% solution) | 20 ml |
| Ethylenediaminetetraacetic acid | 4 g |
| Hydrosulfite | 5 g |
| (made up to one liter with water) | |

The maximum color forming density of the sample obtained was measured. The results are shown in Table 2. The dye residual percentage at the maximum density was determined as follows:

Dye residual percentage =

$$\frac{\text{Density obtained by processing with fatigued bleach-fixing solution}}{\text{Density obtained by processing with new bleach-fixing solution}} \times 100$$

TABLE 2

| Sample No. | Coupler No. | Density (with new bleachfixing solution) | Density (with fatigued bleachfixing solution) | Dye residual percentage (%) |
|---|---|---|---|---|
| 12 | C-1 | 1.95 | 1.46 | 75 |
| 13 | Control coupler(A) | 2.15 | 2.06 | 96 |
| 14 | Control coupler(B) | 2.24 | 2.13 | 95 |
| 15 | Control coupler(C) | 2.16 | 2.03 | 94 |
| 16 | Control coupler(D) | 2.20 | 2.11 | 96 |
| 17 | Control coupler(E) | 2.28 | 2.21 | 97 |
| 18 | Exemplary coupler(4) | 2.15 | 2.06 | 96 |
| 19 | Exemplary coupler(6) | 2.18 | 2.09 | 96 |
| 20 | Exemplary coupler(7) | 2.25 | 2.18 | 97 |
| 21 | Exemplary coupler(8) | 2.75 | 2.64 | 96 |
| 22 | Exemplary | 2.15 | 2.08 | 97 |

TABLE 2-continued

| Sample No. | Coupler No. | Density (with new bleachfixing solution) | Density (with fatigued bleachfixing solution) | Dye residual percentage (%) |
|---|---|---|---|---|
| | coupler(10) | | | |

From Table 2, it could be understood that the samples employing the couplers according to the present invention (Sample No. 18–22) fade little in cyan dyes similarly as in samples employing Control couplers (A)–(E), although the sample employing the Naphthol coupler (C-1) is markedly great in fading of the cyan coupler by processing with the fatigued bleach-fixing solution.

EXAMPLE 3

On a transparent polyester base applied with subbing treatment, the respective layers shown below were provided successively from the base to prepare respective sample with the constitutions as shown below in Table 3.

First layer (halation preventive layer):

An aqueous gelatin solution containing black colloid silver was applied at a proportion of 0.5 g/m² so as to give a dry film thickness of 3.0μ.

Second layer (intermediate layer):

An aqueous gelatin solution was applied so as to give a dry film thickness of 1.0μ.

Third layer (red-sensitive low sensitivity silver halide emulsion layer):

A silver iodobromide emulsion (a mixture of a silver iodobromide emulsion with a mean grain size of 0.6μ, containing 4 mole % of silver iodide and a silver iodobromide emulsion with a mean grain size of 0.3μ, containing 4 mole % of silver iodide mixed at a ratio of 2:1) was chemically sensitized with gold and a sulfur sensitizer, and further, as red-sensitive sensitizing dyes, anhydrous 9-ethyl-3,3'-di-(3-sulfopropyl)-4,5,4'5'-dibenzothiacarbocyanine hydroxide: anhydrous 5,5'-dichloro-9-ethyl-3,3'-di-(3-sulfobutyl)thiacarbocyanine hydroxide: and anhydrous 2-[2-{(5-chloro-3-ethyl-2(3H)-benzothiazolindene)methyl}-1-butenyl-5-chloro-3-(4-sulfobutyl)]benzoxazolium were added, followed by addition of 1.0 g of 4-hydroxy-6-methyl-1,3,3a,7-tetrazaindene and 20.0 mg of 1-phenyl-5-mercaptotetrazole, to obtain a red-sensitive low sensitivity emulsion.

Subsequently, a cyan coupler, a DIR compound, a colored cyan coupler, an antifoggant and a high boiling solvent were added into 150 ml of ethyl acetate, dissolved by heating, and the resultant solution was added into 550 ml of an aqueous 7.5% gelatin solution containing 5 g of sodium triisopropylnaphthalene sulfonate and emulsified by a colloid mill. The emulsion was heated to remove ethyl acetate and mixed with the above red-sensitive low sensitivity emulsion, and the mixture was applied so as to give a dry film thickness of 4.0μ (containing 100 g of gelatin per mole of silver halide).

Fourth layer (red-sensitive high sensitivity silver halide emulsion):

A silver iodobromide emulsion (having a mean grain size of 1.2μ, containing 7 mole % of silver iodide) was chemically sensitized with gold and a sulfur sensitizer and further, a red-sensitive sensitizing dyes, anhydrous 9-ethyl-3,3'-di-(3-sulfopropyl)-4,5,4',5'-dibenzothiacarbocyanine hydroxide; anhydrous 3,3'-dichloro-9-ethyl-3,3'-di-(3-sulfobutyl)thiacarbocyanine hydroxide; and anhydrous 2-[2-{(5-chloro-3-ethyl-2(3H)-benzothiazolidene)methyl}-1-butenyl-5-chloro-3-(4-sulfobutyl)]-benzoxazolium were added, followed by addition of 1.0 g of 4-hydroxy-6-methyl-1,3,3a,7-tetrazaindene and 10.0 mg of 1-phenyl-5-mercaptotetrazole, to obtain a red-sensitive high sensitivity emulsion.

Further, a cyan coupler, a DIR compound, an antifoggant and a high boiling solvent were added into 60 ml of ethyl acetate, dissolved by heating, and the resultant solution was added into 30 ml of an aqueous 7.5% gelatin solution containing 1.5 g of sodium triisopropylnaphthalene sulfonate and emulsified by a colloid mill. The emulsion was mixed with the above red-sensitive high sensitivity emulsion, and the mixture was applied so as to give a dry film thickness of 2.0μ (containing 100 g of gelatin per mole of silver halide).

Fifth layer (intermediate layer):

The same as the second layer.

Sixth layer (green-sensitive low sensitivity silver halide emulsion layer):

A silver iodobromide emulsion with a mean grain size of 0.6μ, containing 4 mole % of silver iodide and a silver iodobromide emulsion with a mean grain size of 0.3μ, containing 7 mole % of silver iodide were each chemically sensitized with gold and a sulfur sensitizer, further, as green-sensitive sensitizing dyes, anhydrous 5,5'-dichloro-9-ethyl-3,3'-di-(3-sulfobutyl)oxacarbocyanine hydroxide; anhydrous 3,3'-diphenyl-9-ethyl-3,3'-di-(3-sulfobutyl)oxacarbocyanine hydroxide; and anhydrous 9-ethyl-3,3'-di-(3-sulfopropyl)-5,6,5',6'-dibenzoxacarbocyanine hydroxide were added, followed by addition of 1.0 g of 4-hydroxy-6-methyl-1,3,3a,7-tetrazaindene and 20.0 mg of 1-phenyl-5-mercaptotetrazole, to prepare emulsions in a conventional manner. The two kinds of silver halide emulsions thus obtained were mixed at a ratio of 1:1 to give a green-sensitive low sensitivity silver halide emulsion.

Further, a magenta coupler, a DIR compound, a colored magenta coupler, an antifoggant and a high boiling solvent were added into 240 ml of ethyl acetate, dissolved by heating, and the resultant solution was added into an aqueous 7.5% gelatin solution containing sodium triisopropylnaphthalene sulfonate and emulsified by a colloid mill. The emulsion was mixed with the above green-sensitive low sensitivity emulsion, and the mixture was applied so as to give a dry film thickness of 4.0μ (containing 100 g of gelatin per mole of silver halide).

Seventh layer (green-sensitive high sensitivity silver halide emulsion layer):

A silver iodobromide emulsion (having a mean grain size of 1.2μ, containing 7 mole % of silver iodide) was chemically sensitized with gold and a sulfur sensitizer, and further, as green-sensitive sensitizing dyes, anhydrous 5,5'-dichloro-9-ethyl-3,3'-di(3-sulfobutyl)oxacarbo-cyanine hydroxide; anhydrous 5,5'-diphenyl-9-ethyl-3,3'-di(3-sulfobutyl)oxacarbocyanine hydroxide; and anhydrous 9-ethyl-3,3'-di-(3-sulfopropyl)-5,6,5'6'-dibenzoxa-carbocyanine hydroxide were added, followed by addition of 1.0 g of 4-hydroxy-6-methyl-1,3,3a,7-tetrazaindene and 10.0 mg of 1-phenyl-5-mercaptoterazole, to obtain a green-sensitive high sensitivity silver halide emulsion.

Further, a magenta coupler, a DIR compound, a colored magenta coupler, an antifoggant and a high boiling solvent were added into 200 ml of ethyl acetate, dissolved by heating, and the resultant solution was added into an aqueous 7.5% gelatin solution containing sodium triisopropylnaphthalene sulfonate and emulsified by a colloid mill. The emulsion was mixed with the above green-sensitive high sensitivity emulsion, and the mixture was applied so as to give a dry film thickness of 2.0μ (containing 100 g of gelatin per mole of silver halide).

Eighth layer (intermediate layer):
The same as the second layer.

Ninth layer (yellow filter layer):
Into an aqueous gelatin solution containing yellow colloid silver dispersed therein was added a dispersion having a solution of 3 g of 2,3-di-t-octylhydroquinone and 1.5 g of di-2-ethylhexylphthalate dissolved in 10 ml of ethyl acetate dispersed in an aqueous gelatin solution containing 0.3 g of sodium triisopropylnaphthalene sulfonate, and the mixture was applied at such a proportion that the amount of gelatin is 0.9 g/m² and the amount of 2,5-di-t-octylhydroquinone is 0.10 g/m², so as to give a dry film thickness of 1.2μ.

Tenth layer (blue sensitive low sensitivity silver halide emulsion layer):
A silver iodobromide emulsion (having a mean grain size of 0.6μ, containing 6 mole % of silver iodide) was chemically sensitized with gold and a sulfur sensitizer and, further, as the sensitizing dye, anhydrous 5,5'-dimethoxy-3,3'-di(3-sulfopropyl)thiacyanine hydroxide was added, followed by controlling in a conventional manner with addition of 1.0 g of 4-hydroxy-6-methyl-1,3,3a,7-tetrazaindene and 20.0 mg of 1-phenyl-5-mercaptotetrazole, to prepare a blue-sensitive low sensitivity silver halide emulsion.

Further, a yellow coupler and a high boiling solvent were added into 300 ml of ethyl acetate, dissolved by heating, and the solution was added into an aqueous 7.5% gelatin solution containing sodium triisopropylnaphthalene sulfonate and emulsified by a colloid mill. To the resultant emulsion was added the above blue-sensitive low sensitivity emulsion and the mixture was appied so as to give a dry film thickness of 4.0μ (containing 240 g of gelatin per mole of silver halide).

Eleventh layer (blue-sensitive high sensitivity silver halide emulsion layer):
A silver iodobromide emulsion (having a mean grain size of 1.2μ, containing 7 mole % of silver iodide) was chemically sensitized with gold and a sulfur sensitizer and, further, as the sensitizing dye, anhydrous 5,5'-dimethoxy-3,3'-di-(3-sulfopropyl)thiacyanine hydroxide, followed by controlling in a conventional manner with addition of 1.0 g of 4-hydroxy-6-methyl-1,3,3a,7-tetrazaindene and 10.0 mg of 1-phenyl-5-mercaptotetrazole, to prepare a blue sensitive high sensitivity silver halide emulsion.

Further, a yellow coupler and a high boiling solvent were added into 240 ml of ethyl acetate, dissolved by heating, and the solution was added into an aqueous 7.5% gelatin solution containing sodium triisopropylnaphthalene fulfonate and emulsified by a colloid mill. To the resultant emulsion was added the above blue-sensitive high sensitivity emulsion and the mixture was appied so as to give a dry film thickness of 2.0μ (containing 160 g of gelatin per mole of silver halide).

Twelfth layer (intermediate layer):
A high boiling solvent and a UV-ray absorber were added in 2 ml of ethyl acetate, and the solution was added into an aqueous 7.5% gelatin solution containing sodium triisopropylnaphthalene sulfonate and emulsified by a colloid mill. The emulsion was applied at a proportion of 1.0 g/m² of gelatin so as to give a dry film thickness of 1.0μ.

Thirteenth layer (protective layer):
An aqueous gelatin solution containing 4 g of gelatin and 0.2 g of 1,2-bisvinylsulfonylethane per 100 ml was applied at a proportion of 1.3 g/m² so as to give a dry film thickness of 1.2μ.

TABLE 3

| | | Example No. 23 | | | | | |
|---|---|---|---|---|---|---|---|
| | | Coupler No. Amount added | High boiling solvent Amount added | DIR coupler Amount added | Colored coupler Amount added | Antifoggant Amount added | UV-ray Absorber Amount added |
| 13th layer | (protective layer) | | | | | | |
| 12th layer | (Intermediate layer) | | HBS-9 2 | | | | U-5 2 |
| 11th layer | (Blue-sensitive high sensitivity layer) | Y-3 11 | HBS-9 50 | | | | |
| 10th layer | (Blue-sensitive low sensitivity layer) | Y-3 34 | HBS-9 50 | | | | |
| 9th layer | (Yellow filter layer) | | | | | | |
| 8th layer | (Intermediate layer) | | | | | | |
| 7th layer | (Green-sensitive high sensitivity layer) | M-3 1.0 | HBS-26 100 | D-5 0.04 | CM-3 0.3 | A-1 1.8 | |
| 6th layer | (Green-sensitive low sensitivity layer) | M-1 7.9 | HBS-26 100 | D-6 0.4 | CM-3 0.8 | A-1 0.5 | |
| 5th layer | (Intermediate layer) | | HBS-9 0.06 | | | A-1 0.06 | |
| 4th layer | (Red-sensitive high sensitivity layer) | C-2 1.8 | HBS-9 100 | D-13 0.4 | | A-1 0.5 | |
| 3rd layer | (Red-sensitive low sensitivity layer) | (6) 10.0 | HBS-9 100 | D-2 0.4 | CC-3 0.3 | A-1 0-.5 | |
| 2nd layer | (Intermediate layer) | | | | | | |
| 1st layer | (Halation preventive layer) | | | | | | |
| Support | | | | | | | |

In the above Table 3, the amounts added indicate the amounts added per mole of silver halide. Couplers, DIR couplers and colored couplers were given in mole %; high boiling solvents and antifoggants in % by weight based on the amount of coupler; UV-ray absorber in weight per unit m²; and the high boiling solvent used in the twelfth layer was used in the same weight (g) (per m²) as the UV-ray absorber. The antifoggant used in the fifth layer represents the weight per m², and the high boiling solvent was used in the same amount as the antifoggant.

The respective samples were processed with the constitutions as shown in the above Table 3, following the processing steps as shown in Example 1, and a result, they were found to be light-sensitive silver halide color photographic materials having stable color balance.

EXAMPLE 4

Spectral absorption characteristics of the respective dyes formed by employing C-1, Control coupler (A), and Exemplary coupler (6) of Samples No. 1, No. 2 and No. 8 obtained in Example 1 are shown in the drawing.

From this drawing, it can be understood that the dye formed from the coupler (6) of the present invention has the maximum absorption wavelength at the longer wavelength side, while being sharply cut off in absorption on the shorter wavelength side, thus proving to be a preferable dye in color reproduction.

EXAMPLE 5

As shown in Table 4, each 0.1 mole of the cyan couplers of the present invention was weighed per one mole of silver, and dibutyl phthalate (as high boiling solvent) as the coupler and ethyl acetate were added there to, in an amount equivalent to and 3-fold of the amount of the coupler, respectively, and the coupler was completely dissolved in these solvents by heating to 60° C. Also, for comparison, each 0.1 mole of Control couplers known in the art was weighed per 1 mole of silver, and dibutyl phthalate as the coupler and ethyl acetate were added thereto, in an amount equivalent to and 3-fold of the amount of the Control coupler, respectively, and the coupler was completely dissolved in these solvents by heating to 60° C. The solution was mixed with 1200 ml of an aqueous 5% gelatin solution containing 120 ml of an aqueous 5% solution of Alkanol B (alkylnaphthalene sulfonate: produced by Du Pont Co.), dispersed by means of a ultrasonic dispersing machine to obtain an emulsion. Then, the dispersion was added to 4 kg of a red-sensitive silver iodobromide emulsion (containing 7 mole % of silver iodide), followed by addition of 120 ml of a 2% solution of 1,2-bis(-vinylsulfonyl)ethane (water:methanol=1:1) as film hardener, and the resultant mixture was applied on a transparent polyester base subjected to subbing treatment and dried to give a sample having a stable coated film (coated silver quantity: 15 mg/100 cm²).

The sample thus obtained was subjected to wedge exposure in a conventional manner, and the following developing processing was performed. The results are shown in Table 4.

Sensitivity and the maximum color forming density were measured by PDA-65 Model Densitometer produced by Konishiroku Photo Industry Co., Ltd.

| [Processing step] (38° C.) | Processing time |
|---|---|
| Color developing | 3 min. 15 sec. |
| Bleaching | 1 min. 30 sec. |
| Water washing | 3 min. 15 sec. |
| Fixing | 6 min. 30 sec. |

-continued

| [Processing step] (38° C.) | Processing time |
|---|---|
| Water washing | 3 min. 15 sec. |
| Stabilizing bath | 1 min. 30 sec. |

The processing liquors employed in the processing steps had the compositions as shown below.

| [Color developing solution] | |
|---|---|
| 4-Amino-3-methyl-N—ethyl-N— (β-hydroxyethyl)-aniline sulfate | 4.75 g |
| Anhydrous sodium sulfite | 4.25 g |
| Hydroxyamine ½ sulfate | 2.0 g |
| Anhydrous potassium carbonate | 37.5 g |
| Sodium bromide | 1.3 g |
| Trisodium nitrilotriacetate (monohydrate) | 2.5 g |
| Potassium hydroxide | 1.0 g |
| (made up to one liter with water and adjusted to pH 10.0 with potassium hydroxide) | |
| [Bleaching solution] | |
| Ferric ammonium ethylenediaminetetraacetate | 100.0 g |
| Diammonium ethylenediaminetetraacetate | 10.0 g |
| Ammonium bromide | 150.0 g |
| Glacial acetic acid | 10.0 ml |
| (made up to one liter with water and adjusted to pH 6.0 with aqueous ammonia) | |
| [Fixing solution] | |
| Ammonium thiosulfate (50% aqueous solution) | 162 ml |
| Anhydrous sodium sulfite | 12.4 g |
| (made up to one liter with water and adjusted to pH 6.5 with acetic acid) | |
| [Stabilizing solution] | |
| Formalin (37% aqueous solution) | 5.0 ml |
| Konidax (produced by Konishiroku Photo Industry Co., Ltd.) | 7.5 ml |
| (made up to one liter with water) | |

TABLE 4

| Sample No. | Coupler No. | Relative sensitivity | Maximum color forming density | Maximum absorption wavelength | $\Delta\lambda_s$ |
|---|---|---|---|---|---|
| 24 | C-1 | 100 | 1.95 | 696 | 123 |
| 25 | Control coupler(A) | 102 | 2.15 | 689 | 133 |
| 26 | Control coupler(G) | 107 | 2.23 | 686 | 135 |
| 27 | Control coupler(H) | 120 | 2.35 | 689 | 133 |
| 28 | Control coupler(I) | 115 | 2.33 | 685 | 134 |
| 29 | Exemplary coupler(21) | 117 | 2.30 | 689 | 130 |
| 30 | Exemplary coupler(24) | 105 | 2.20 | 690 | 128 |
| 31 | Exemplary coupler(25) | 120 | 2.32 | 690 | 128 |
| 32 | Exemplary coupler(27) | 118 | 2.28 | 691 | 130 |
| 33 | Exemplary coupler(28) | 131 | 2.75 | 690 | 131 |

In the Table, relative sensitivities are represented relative to the sensitivity obtained in Sample No. 24 as 100, the maximum absorption wavelength ($\lambda_{max}$) is the wavelength in the spectral curve at which a maximum density of 1.0 is exhibited, and $\Delta\lambda_s$ is exhibited as a value obtained by subtracting the absorption wavelength on the shorter wavelength side giving a density of 0.2 in the spectral absorption curve.

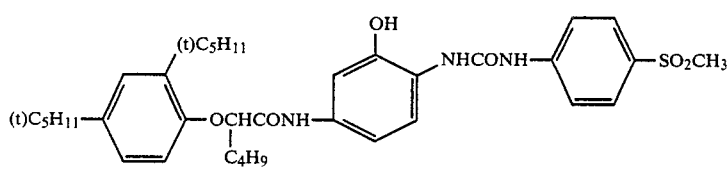

Control coupler (G)

(Compound as disclosed in Japanese Unexamined Patent Publication Nos. 204545/1982 and 98731/1983)

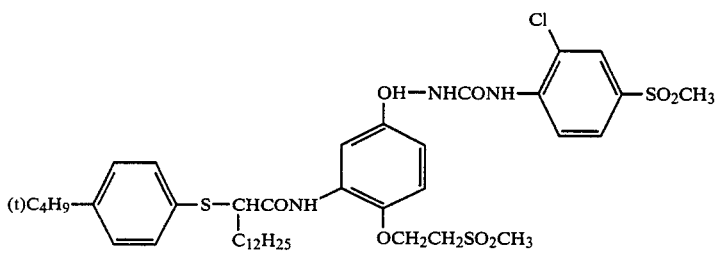

Control coupler (H)

(Compound as disclosed in Japanese Unexamined Patent Publication No. 204545/1982)

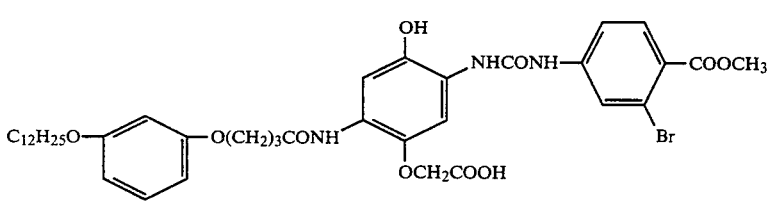

Control coupler (I)

(Compound as disclosed in Japanese Unexamined Patent Publication No. 204545/1982)

As is apparent from Table 4, all of the couplers of the present invention (Sample Nos. 29-33) exhibit sensitivities and maximum color forming densities which are equal to or better than those of Control couplers. As for the maximum absorption wavelength and $\Delta\lambda_s$, as compared with Control couplers (A) and (G)-(I), the maximum absorption wavelength approximately at least equal to those of Control couplers, while all of the samples were less in $\Delta\lambda_s$, thus giving favorable results in color reproduction. Particularly, the difference in these numerical values is a great siginificant difference when its effect extending to the region of green light is taken into consideration, whereby a great improvement effect could be brought about in view of color reproduction.

EXAMPLE 6

The samples obtained in Example 5 were subjected to wedge exposure and then applied with the developing processing of Example 5. On the other hand, processing with a bleach-fixing solution changed to have the following composition was performed, and fading of the cyan dye obtained by processing with a fatigued bleach-fixing solution was examined.

| [Bleach-fixing solution] | |
|---|---|
| Ferric ammonium ethylenediaminetetraacetate | 50 g |
| Ammonium sulfite (40% solution) | 50 ml |
| Ammonium thiosulfate (70% solution) | 140 ml |
| Aqueous ammonia (28% solution) | 20 ml |
| Ethylenediaminetetraacetic acid | 4 g |
| Hydrosulfite | 5 g |
| (made up to one liter with water) | |

The maximum color forming density of the sample obtained was measured. The results are shown in Table 5. The dye residual percentage at the maximum density was determined as follows:

Dye residual percentage =

$$\frac{\text{Density obtained by processing with fatigued bleach-fixing solution}}{\text{Density obtained by processing with new bleach-fixing solution}} \times 100$$

TABLE 5

| Sampler No. | Coupler No. | Density (with new bleachfixing solution) | Density (with fatigued bleachfixing solution) | Dye residual percentage (%) |
|---|---|---|---|---|
| 34 | C-1 | 1.95 | 1.46 | 75 |
| 35 | Control coupler(A) | 2.15 | 2.06 | 96 |
| 36 | Control coupler(G) | 2.23 | 2.16 | 97 |
| 37 | Control coupler(H) | 2.35 | 2.26 | 96 |
| 38 | Control coupler(I) | 2.33 | 2.26 | 97 |
| 39 | Exemplary coupler(21) | 2.30 | 2.21 | 96 |
| 40 | Exemplary coupler(24) | 2.20 | 2.13 | 97 |
| 41 | Exemplary coupler(25) | 2.32 | 2.25 | 97 |
| 42 | Exemplary coupler(27) | 2.28 | 2.19 | 96 |
| 43 | Exemplary coupler(28) | 2.75 | 2.67 | 97 |

From Table 5, it could be understood that the samples employing the couplers according to the present invention (Sample Nos. 39-43) fade little in cyan dyes similarly as in samples employing Control couplers (A) and (G)-(I), although the sample employing the Naphthol coupler (C-1) is markedly great in fading of the cyan coupler by processing with the fatigued bleach-fixing solution.

EXAMPLE 7

On a transparent polyester base applied with subbing treatment, the respective layers shown below were provided successively from the base to prepare respective samples with the constitutions as shown below in Table 6.

First layer (halation preventive layer):

An aqueous gelatin solution containing black colloid silver was applied at a proportion of 0.5 g/m² so as to give a dry film thickness of 3.0μ.

Second layer (intermediate layer):

An aqueous gelatin solution was applied so as to give a dry film thickness of 1.0μ.

Third layer (red-sensitive low sensitivity silver halide emulsion layer):

A silver iodobromide emulsion (a mixture of a silver iodobromide emulsion with a mean grain size of 0.6μ, containing 4 mole % of silver iodide and a silver iodobromide emulsion with a mean grain size of 0.3μ, containing 4 mole % of silver iodide mixed at a ratio of 2:1) was chemically sensitized with gold and a sulfur sensitizer, and further, as red-sensitive sensitizing dyes, anhydrous 9-ethyl-3,3'-di-(3-sulfopropyl)-4,5,4'5'-dibenzothiacarbocyanine hydroxide: anhydrous 5,5'-dichloro-9-ethyl-3,3'-di-(3-sulfobutyl)thiacarbocyanine hydroxide: and anhydrous 2-[2-{(5-chloro-3-ethyl-2(3H)-benzothiazolindene)methyl}-1-butenyl-5-chloro-3-(4-sulfobutyl)]benzoxazolium were added, followed by addition of 1.0 g of 4-hydroxy-6-methyl-1,3,3a,7-tetrazaindene and 20.0 mg of 1-phenyl-5-mercaptotetrazole, to obtain a red-sensitive low sensitivity emulsion.

Subsequently, a cyan coupler, a DIR compound, a colored cyan coupler, an antifoggant and a high boiling solvent were added into 150 ml of ethyl acetate, dissolved by heating, and the resultant solution was added into 550 ml of an aqueous 7.5% gelatin solution containing 5 g of sodium triisopropylnaphthalene sulfonate and emulsified by a colloid mill. The emulsion was heated to remove ethyl acetate and mixed with the above red-sensitive low sensitivity emulsion, and the mixture was applied so as to give a dry film thickness of 4.0μ (containing 100 g of gelatin per mole of silver halide).

Fourth layer (red-sensitive high sensitivity silver halide emulsion):

A silver iodobromide emulsion (having a mean grain size of 1.2μ, containing 7 mole % of silver iodide) was chemically sensitized with gold and a sulfur sensitizer and further, as red-sensitive sensitizing dyes, anhydrous 9-ethyl-3,3'-di-(3-sulfopropyl)-4,5,4',5'-dibenzothiacarbocyanine hydroxide; anhydrous 3,3'-dichloro-9-ethyl-3,3'-di-(3-sulfobutyl)thiacarbocyanine hydroxide; and anhydrous 2-[2-{(5-chloro-3-ethyl-2(3H)-benzothiazolidene)methyl}-1-butenyl-5-chloro-3-(4-sulfobutyl)]-benzoxazolium were added, followed by addition of 1.0 g of 4-hydroxy-6-methyl-1,3,3a,7-tetrazaindene and 10.0 mg of 1-phenyl-5-mercaptotetrazole, to obtain a red-sensitive high sensitivity emulsion.

Further, a cyan coupler, a DIR compound, an antifoggant and a high boiling solvent were added into 60 ml of ethyl acetate, dissolved by heating, and the resultant solution was added into 30 ml of an aqueous 7.5% gelatin solution containing 1.5 g of sodium triisopropylnaphthalene sulfonate and emulsified by a colloid mill. The emulsion was mixed with the above red-sensitive high sensitivity emulsion, and the mixture was applied so as to give a dry film thickness of 2.0μ (containing 100 g of gelatin per mole of silver halide).

Fifth layer (intermediate layer):
The same as the second layer.

Sixth layer (green-sensitive low sensitivity silver halide emulsion layer):

A silver iodobromide emulsion with a mean grain size of 0.6μ, containing 4 mole % of silver iodide and a silver iodobromide emulsion with a mean grain size of 0.3μ, containing 7 mole % of silver iodide were each chemically sensitized with gold and a sulfur sensitizer, further, as green-sensitive sensitizing dyes, anhydrous 5,5'-dichloro-9-ethyl-3,3'-di-(3-sulfobutyl) oxacarbocyanine hydroxide; anhydrous 3,3'-diphenyl-9-ethyl-3,3'-di-(3-sulfobutyl)oxacarbocyanine hydroxide; and anhydrous 9-ethyl-3,3'-di-(3-sulfopropyl)-5,6,5',6'-dibenzoxacarbocyanine hydroxide were added, followed by addition of 1.0 g of 4-hydroxy-6-methyl-1,3,3a,7-tetrazaindene and 20.0 mg of 1-phenyl-5-mercaptotetrazole, to prepare emulsions in a conventional manner. The two kinds of silver halide emulsions thus obtained were mixed at a ratio of 1:1 to give a green-sensitive low sensitivity silver halide emulsion.

Further, a magenta coupler, a DIR compound, a colored magenta coupler, an antifoggant and a high boiling solvent were added into 240 ml of ethyl acetate, dissolved by heating, and the resultant solution was added into an aqueous 7.5% gelatin solution containing sodium triisopropylnaphthalene sulfonate and emulsified by a colloid mill. The emulsion was mixed with the above green-sensitive low sensitivity emulsion, and the mixture was applied so as to give a dry film thickness of 4.0μ (containing 100 g of gelatin per mole of silver halide).

Seventh layer (green-sensitive high sensiivity silver halide emulsion layer):

A silver iodobromide emulsion (having a mean grain size of 1.2μ, containing 7 mole % of silver iodide) was chemically sensitized with gold and a sulfur sensitizer, and further, as green-sensitive sensitizing dyes, anhydrous 5,5'-dichloro-9-ethyl-3,3'-di(3-sulfobutyl)oxacarbo-cyanine hydroxide; anhydrous 5,5'-diphenyl-9-ethyl-3,3'-di(3-sulfobutyl)oxacarbocyanine hydroxide; and anhydrous 9-ethyl-3,3'-di-(3-sulfopropyl)-5,6,5',6'-dibenzoxa-carbocyanine hydroxide were added, followed by addition of 1.0 g of 4-hydroxy-6-methyl-1,3,3a,7-tetrazaindene and 10.0 mg of 1-phenyl-5-mercaptoterazole, to obtain a green-sensitive high sensitivity silver halide emulsion.

Further, a magenta coupler, a DIR compound, a colored magenta coupler, an antifoggant and a high boiling solvent were added into 200 ml of ethyl acetate, dissolved by heating, and the resultant solution was added into an aqueous 7.5% gelatin solution containing sodium triisopropylnaphthalene sulfonate and emulsified by a colloid mill. The emulsion was mixed with the above green-sensitive high sensitivity emulsion, and the mixture was applied so as to give a dry film thickness of 2.0μ (containing 100 g of gelatin per mole of silver halide).

Eighth layer (intermediate layer):
The same as the second layer.

Ninth layer (yellow filter layer):

Into an aqueous gelatin solution containing yellow colloid silver dispersed therein was added a dispersion having a solution of 3 g of 2,3-di-t-octylhydroquinone and 1.5 g of di-2-ethylhexylphthalate dissolved in 10 ml of ethyl acetate dispersed in an aqueous gelatin solution containing 0.3 g of sodium triisopropylnaphthalene sulfonate, and the mixture was applied at such a proportion that the amount of gelatin is 0.9 g/m² and the amount of 2,5-di-t-octylhydroquinone is 0.10 g/m², so as to give a dry film thickness of 1.2μ.

Tenth layer (blue sensitive low sensitivity silver halide emulsion layer):

A silver iodobromide emulsion (having a mean grain size of 0.6μ, containing 6 mole % of silver iodide) was chemically sensitized with gold and a sulfur sensitizer and, further, as the sensitizing dye, anhydrous 5,5'-dimethoxy-3,3'-di(3-sulfopropyl)thiacyanine hydroxide was added, followed by controlling in a conventional manner with addition of 1.0 g of 4-hydroxy-6-methyl-1,3,3a,7-tetrazaindene and 20.0 mg of 1-phenyl-5-mercaptotetrazole, to prepare a blue-sensitive low sensitivity silver halide emulsion.

Further, a yellow coupler and a high boiling solvent were added into 300 ml of ethyl acetate, dissolved by heating, and the solution was added into an aqueous 7.5% gelatin solution containing sodium triisopropylnaphthalene sulfonate and emulsified by a colloid mill. To the resultant emulsion was added the above blue-sensitive low sensitivity emulsion and the mixture was appied so as to give a dry film thickness of 4.0μ (containing 240 g of gelatin per mole of silver halide).

Eleventh layer (blue-sensitive high sensitivity silver halide emulsion layer):

A silver iodobromide emulsion (having a mean grain size of 1.2μ, containing 7 mole % of silver iodide) was chemically sensitized with gold and a sulfur sensitizer and, further, as the sensitizing dye, anhydrous 5,5'-dimethoxy-3,3'-di-(3-sulfopropyl)thiacyanine hydroxide, followed by controlling in a conventional manner with addition of 1.0 g of 4-hydroxy-6-methyl-1,3,3a,7-tetrazaindene and 10.0 mg of 1-phenyl-5-mercaptotetrazole, to prepare a blue sensitive high sensitivity silver halide emulsion.

Further, a yellow coupler and a high boiling solvent were added into 240 ml of ethyl acetate, dissolved by heating, and the solution was added into an aqueous 7.5% gelatin solution containing sodium triisopropylnaphthalene fulfonate and emulsified by a colloid mill. To the resultant emulsion was added the above blue-sensitive high sensitivity emulsion and the mixture was appied so as to give a dry film thickness of 2.0μ (containing 160 g of gelatin per mole of silver halide).

Twelfth layer (intermediate layer):

A high boiling solvent and a UV-ray absorber were added in 2 ml of ethyl acetate, and the solution was added into an aqueous 7.5% gelatin solution containing sodium triisopropylnaphthalene sulfonate and emulsified by a colloid mill. The emulsion was applied at a proportion of 1.0 g/m² of gelatin so as to give a dry film thickness of 1.0μ.

Thirteenth layer (protective layer):

An aqueous gelatin solution containing 4 g of gelatin and 0.2 g of 1,2-bisvinylsulfonylethane per 100 ml was applied at a proportion of 1.3 g/m² so as to give a dry film thickness of 1.2μ.

TABLE 6

| | | Example No. 44 | | | | | |
|---|---|---|---|---|---|---|---|
| | | Coupler No. Amount added | High boiling solvent Amount added | DIR coupler Amount added | Colored coupler Amount added | Antifoggant Amount added | UV-ray Absorber Amount added |
| 13th layer | (Protective layer) | | | | | | |
| 12th layer | (Intermediate layer) | | HBS-9 2 | | | | U-5 2 |
| 11th layer | (Blue-sensitive high sensitivity layer) | Y-3 11 | HBS-9 50 | | | | |
| 10th layer | (Blue-sensitive low sensitivity layer) | Y-3 34 | HBS-9 50 | | | | |
| 9th layer | (Yellow filter layer) | | | | | | |
| 8th layer | (Intermediate layer) | | | | | | |
| 7th layer | (Green-sensitive high sensitivity layer) | M-3 1.0 | HBS-26 100 | D-5 0.04 | CM-3 0.3 | A-1 1.8 | |
| 6th layer | (Green-sensitive low sensitivity layer) | M-1 7.9 | HBS-26 100 | D-6 0.4 | CM-3 0.8 | A-1 0.5 | |
| 5th layer | (Intermediate layer) | | HBS-9 0.06 | | | A-1 0.06 | — |
| 4th layer | (Red-sensitive high sensitivity layer) | C-2 1.8 | HBS-9 100 | D-12 0.4 | | A-1 0.5 | |
| 3rd layer | (Red-sensitive low sensitivity layer) | (6) 10.0 | HBS-9 100 | D-2 0.4 | CC-3 0.3 | A-1 0-.5 | |
| 2nd layer | (Intermediate layer) | | | | | | |
| 1st layer | (Halation preventive layer) | | | | | | |
| Support | | | | | | | |

In the above Table 6, the amounts added indicate the amounts added per mole of silver halide. Couplers, DIR couplers and colored couplers were given in mole %; high boiling solvents and antifoggants in % by weight based on the amount of coupler; UV-ray absorber in weight per unit m²; and the high boiling solvent used in the twelfth layer was used in the same weight (g) (per m²) as the UV-ray absorber. The antifoggant used in the fifth layer represents the weight per m², and the high boiling solvent was used in the same amount as the antifoggant.

The respective samples were processed with the constitutions as shown in the above Table 6, following the processing steps as shown in Example 1, and a result, they were found to be light-sensitive silver halide color photographic materials having stable color balance.

EXAMPLE 8

Spectral absorption characteristics of the respective dyes formed by employing C-1, Control coupler (A), and Exemplary coupler (24) of Samples No. 1, No. 25 and No. 30 obtained in Example 5 are shown in the drawing.

From this drawing, it can be understood that the dye formed from the coupler (24) of the present invention has the maximum absorption wavelength at the longer wavelength side, while being sharply cut off in absorption on the shorter wavelength side, thus proving to be a preferable dye in color reproduction.

We claim:

1. A light-sensitive silver halide color photographic material, which comprises containing a cyan coupler for photography represented by the Formula (I) shown below in the light-sensitive emulsion;

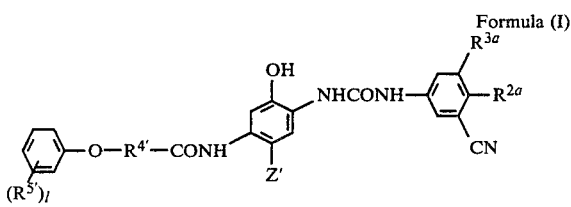

wherein $R^{4'}$ represents an alkylene group having 1 to 20 carbon atoms; $R^{5'}$ represents a halogen atom, a hydroxy group, an alkyl group having 1 to 20 carbon atoms, an alkoxy group, an alkylsulfonamide group, an arylsulfonamide group, an alkylsulfamoyl group, an arylsulfamoyl group, an alkylsulfonyl group, an arylsulfonyl group, a cycloalkyl group, or an alkoxycarbonyl group; l represents an integer of 1 to 4, when l is 2 or more, $R^{5'}$ may be either identical or different; $R^{2a}$ and $R^{3a}$ each represent a hydrogen atom or a halogen atom, at least one of $R^{2a}$ and $R^{3a}$ being a halogen atom; and $Z'$ represents a hydrogen atom or a group eliminable during the coupling reaction with the oxidized product of a color developing agent.

2. The light-sensitive silver halide color photographic material according to claim 1, wherein $R^{5'}$ in Formula (I) represents a hydroxy group, an alkyl group having 1 to 20 carbon atoms, an arylsulfonyl group or a cycloalkyl group.

3. The light-sensitive silver halide color photographic material according to claim 1, wherein Z in Formula (I) represents a hydrogen atom, a halogen atom, an alkoxy group, an aryloxy group or an arylthio group.

4. The light-sensitive silver halide color photographic material according to claim 1, wherein $R^{2a}$ and $R^{3a}$ in Formula (I) represent a hydrogen atom, a fluorine atom, a chlorine atom or a bromine atom.

5. The light-sensitive silver halide color photographic material according to claim 1, wherein $R^{2a}$ and $R^{3a}$ each represent a hydrogen atom or a chlorine atom; $R^{4'}$ represents an alkylene group having 1 to 20 carbon atoms; $R^{5'}$ represents a hydroxy group or an alkyl group having 1 to 20 carbon atoms; $Z'$ represents a hydrogen atom, a halogen atom or an aryloxy group; at least one of $R^{2a}$ and $R^{3a}$ being a chlorine atom; l is an integer of 1 or 2; when l is 2, both $R^{5'}$ may be either identical or different, provided that the total number of carbon atoms in the alkylene group represented by $R^{4'}$ and the alkyl group represented by $R^{5'}$ is 8 to 25.

6. The light-sensitive silver halide color photographic material according to claim 5, wherein the coupler is one selected from the group consisting of compounds represented by Formulae:

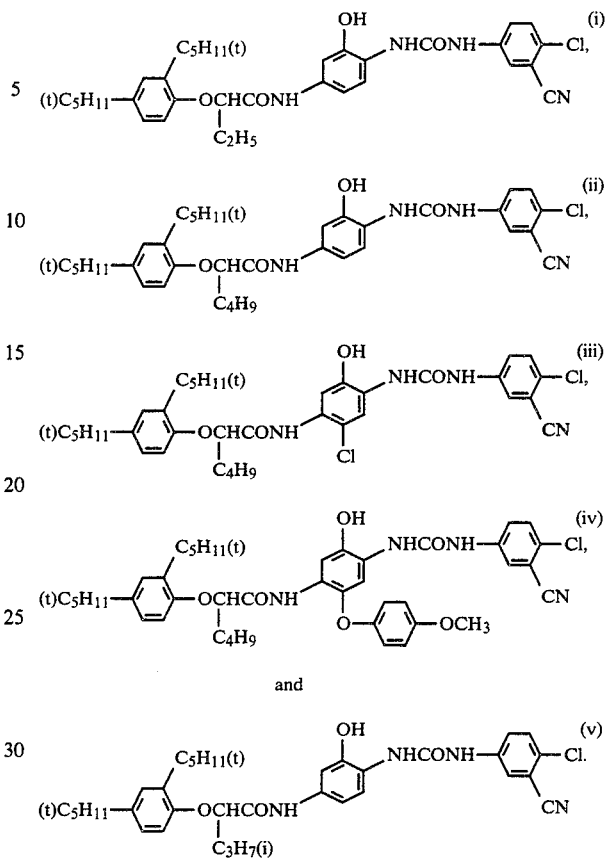

and

7. The light-sensitive silver halide color photographic material according to claim 1, wherein the cyan coupler is contained in an amount of 0,005 to 2 moles per mole of the silver halide.

8. The light-sensitive silver halide color photographic material according to claim 7, wherein the cyan coupler is contained in an amount of 0,01 to 0,5 mole per mole of the silver halide.

9. The light-sensitive silver halide color photographic material according to claim 2, wherein an $R^{5'}$ is cyclopentyl.

10. The light-sensitive silver halide color photographic material according to claim 2, wherein the coupler is

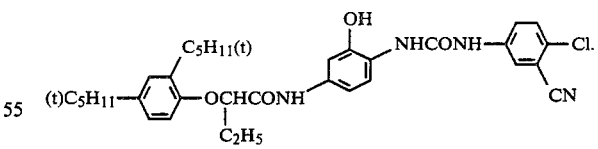

11. The light-sensitive silver halide color photographic material according to claim 1, wherein the coupler is

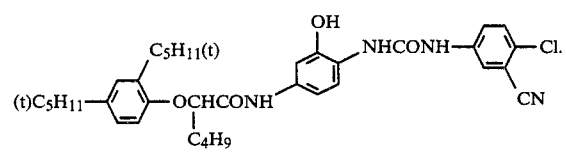

12. The light-sensitive silver halide color photographic material according to claim 2, wherein the coupler is
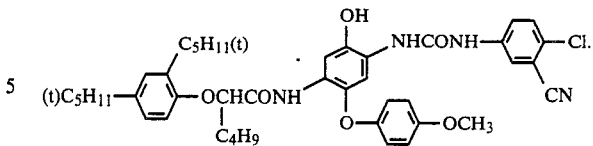
13. The light-sensitive silver halide color photographic material according to claim 2, wherein the coupler is
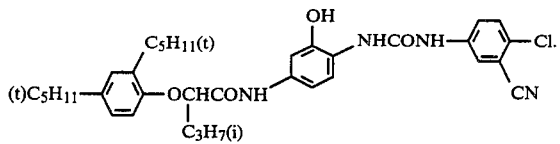
14. The light-sensitive silver halide color photographic material according to claim 2, wherein the coupler is
* * * * *